United States Patent
Burgey et al.

(10) Patent No.: US 7,476,665 B2
(45) Date of Patent: Jan. 13, 2009

(54) BENZODIAZEPINE CGRP RECEPTOR ANTAGONISTS

(75) Inventors: Christopher S. Burgey, Philadelphia, PA (US); Craig A. Stump, Pottstown, PA (US); Theresa M. Williams, Harleysville, NJ (US)

(73) Assignee: Merck & Co., Inc., Rahway, NJ (US)

( * ) Notice: Subject to any disclaimer, the term of this patent is extended or adjusted under 35 U.S.C. 154(b) by 234 days.

(21) Appl. No.: 10/562,297

(22) PCT Filed: Jun. 24, 2004

(86) PCT No.: PCT/US2004/020209

§ 371 (c)(1),
(2), (4) Date: Dec. 22, 2005

(87) PCT Pub. No.: WO2005/013894

PCT Pub. Date: Feb. 17, 2005

(65) Prior Publication Data

US 2006/0135511 A1 Jun. 22, 2006

Related U.S. Application Data

(60) Provisional application No. 60/482,854, filed on Jun. 26, 2003.

(51) Int. Cl.
*A61P 25/06* (2006.01)
*A61K 31/55* (2006.01)
*C07D 401/14* (2006.01)

(52) U.S. Cl. .................. 514/221; 540/502; 540/509

(58) Field of Classification Search ................ 540/502, 540/509; 514/221
See application file for complete search history.

(56) References Cited

FOREIGN PATENT DOCUMENTS

WO WO00/18764 4/2000

*Primary Examiner*—Bruck Kifle
(74) *Attorney, Agent, or Firm*—William Krovatin; John C. Todaro

(57) ABSTRACT

The present invention is directed to compounds of Formula I: I (where variables $R^1$, $R^2$, $R^3$, $R^6$, $R^7$, G, J, Q, T, U, V, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

(I)

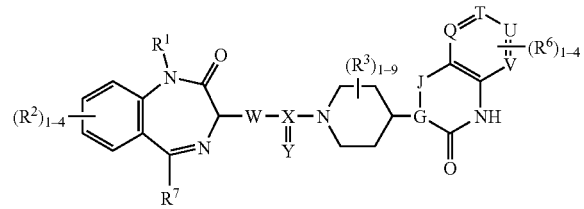

13 Claims, No Drawings

BENZODIAZEPINE CGRP RECEPTOR ANTAGONISTS

CROSS REFERENCE TO RELATED APPLICATIONS

This application is the National Stage of International Application No. PCT/US04/20209, filed 24 Jun. 2004 which claims the benefit under 35 U.S.C. 119(e) of U.S. Provisional Application No. 60/482,854, filed 26 Jun. 2003.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

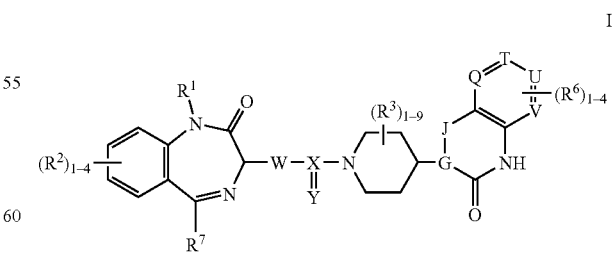

(where variables $R^1$, $R^2$, $R^3$, $R^6$, $R^7$, G, J, Q, T, U, V, W, X and Y are as defined herein) useful as antagonists of CORP receptors and useful in the treatment or prevention of diseases in which the CORP is involved, such as headache, migraine and cluster headache. The invention is also directed to pharmaceutical compositions comprising these compounds and the use of these compounds and compositions in the prevention or treatment of such diseases in which CORP is involved.

DETAILED DESCRIPTION OF THE INVENTION

The present invention is directed to compounds of Formula I:

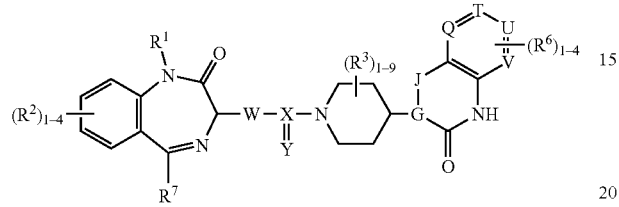

I wherein:
$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$; and
2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$; and
$R^2$ is independently selected from H and:
1) $C_{1-6}$ alkyl,
2) $C_{3-6}$ cycloalkyl,
3) aryl, unsubstituted or substituted with 1-5 substituents where the substituents are independently selected from $R^4$,
4) heteroaryl, unsubstituted or substituted with 1-5 substituents where the substituents are independently selected from $R^4$,
5) heterocycle, unsubstituted or substituted with 1-5 substituents where the substituents are independently selected from $R^4$,
6) $(F)_p C_{1-3}$ alkyl,
7) halogen,
8) $OR^4$,
9) $O(CH_2)_s OR^4$,
10) $CO_2 R^4$,
11) $(CO)NR^{10}R^{11}$,
12) $O(CO)NR^{10}R^{11}$,
13) $N(R^4)(CO)NR^{10}R^{11}$,
14) $N(R^{10})(CO)R^{11}$,
15) $N(R^{10})(CO)OR^{11}$,
16) $SO_2 NR^{10}R^{11}$,
17) $N(R^{10})SO_2 R^{11}$,
18) $S(O)_m R^{10}$,
19) CN,
20) $NR^{10}R^{11}$,
21) $N(R^{10})(CO)NR^4 R^{11}$, and
22) $O(CO)R^4$;
$R^7$ is selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$, i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$,
v) $O(CO)R^4$; and 2) aryl or heteroaryl, unsubstituted or substituted with one or more substituents independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

$R^4$ is selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

$R^5$ is independently selected from H, substituted or unsubstituted $C_1$-$C_6$ alkyl, $C_{3-6}$ cycloalkyl, aryl, heteroaryl, $OR^4$, $N(R^4)_2$, $CO_2R^4$ and $(F)_pC_{1-6}$ alkyl;

W is O, $NR^4$ or $C(R^4)_2$;

X is C or S;

Y is O, $(R^4)_2$, NCN, $NSO_2CH_3$ or $NCONH_2$, or Y is $O_2$ when X is S;

$R^3$ is independently selected from H, substituted or unsubstituted $C_1$-$C_3$ alkyl, CN and $CO_2R^4$;

$R^6$ is independently selected from H and:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from $R^4$;

G-J is selected from: N, $N-C(R^5)_2$, $C=C(R^5)$, $C=N$; $C(R^5)$, $C(R^5)-C(R^5)_2$, $C(R^5)-C(R^5)_2-C(R^5)_2$, $C=C(R^5)-C(R^5)_2$, $C(R^5)-C(R^5)=C(R^5)$, $C(R^5)-C(R^5)_2-N(R^5)$, $C=C(R^5)-N(R^5)$, $C(R^5)-C(R^5)=N$, $C(R^5)-N(R^5)-C(R^5)_2$, $C=N-C(R^5)_2$, $C(R^5)-N=C(R^5)$, $C(R^5)-N(R^5)-N(R^5)-N(R^5)$, $C=N-N(R^5)$, $N-C(R^5)_2-C(R^5)_2$, $N-C(R^5)=C(R^5)$, $N-C(R^5)_2-N(R^5)$, $N-C(R^5)=N$, $N-N(R^5)-C(R^5)_2$ and $N-N=C(R^5)$;

Q, T, U and V are each independently a carbon atom or a nitrogen atom wherein at least one but no more than three of Q, T, U and V are nitrogen atoms, and wherein when any of Q, T, U, or V is a carbon atom it is unsubstituted or substituted where the substituents are independently selected from $R^6$;

p is 0 to 2q+1, for a substituent with q carbons;

m is 0,1 or 2;

n is 0 or 1;

s is 1, 2 or 3;

and pharmaceutically acceptable salts and individual diastereomers thereof.

An embodiment of the present invention includes compounds of the formula Ia:

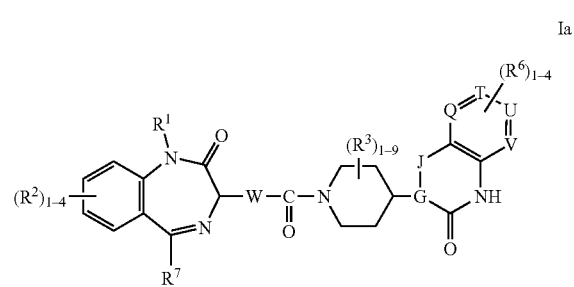

Ia wherein $R^1$, $R^2$, $R^3$, $R^6$, $R^7$, G, J, Q, T, U, V and W are as defined herein; and pharmaceutically acceptable salts and individual diastereomers thereof.

Another embodiment of the present invention includes compounds of the formula Ia, wherein $R^7$ is phenyl, unsubstituted or substituted with one or substituents independently selected from:
a) $C_{1-6}$ alkyl,
b) OH,
c) $OR^5$,
d) halogen,
e) $CO_2R^4$,
f) $S(O)_m R^5$,
g) $N(R^4)_2$, and
j) CN, and wherein $R^1$, $R^2$, $R^3$, $R^6$, G, J, Q, T, U, V and W are as defined herein; and pharmaceutically acceptable salts and individual diastereomers thereof.

Another embodiment of the present invention includes compounds of the formula Ia, wherein $R^7$ is heteroaryl, unsubstituted or substituted with one or substituents independently selected from:
a) $C_{1-6}$ alkyl,
b) OH,
c) $OR^5$,
d) halogen,
e) $CO_2R^4$,
f) $S(O)_m R^5$,
g) $N(R^4)_2$, and
j) CN, and wherein $R^1$, $R^2$, $R^3$, $R^6$, G, J, Q, T, U, V and W are as defined herein; and pharmaceutically acceptable salts and individual diastereomers thereof.

Still another embodiment of the present invention includes compounds of the formula Ia, wherein $R^7$ is selected from H and $C_1$-$C_6$ alkyl, $C_1$-$C_6$ alkenyl, $C_1$-$C_6$ alkynyl, $C_3$-$C_6$ cycloalkyl, unsubstituted or substituted with one or substituents independently selected from:
a) $C_{1-6}$ alkyl,
b) $C_{1-6}$ alkoxy,
c) fluorine,
d) HO,
e) $OR^5$,
f) $CO_2R^4$,
g) $CON(R^4)_2$,
h) $S(O)_m R^5$, and
i) $N(R^4)_2$; and and wherein $R^1$, $R^2$, $R^3$, $R^6$, G, J, Q, T, U, V and W are as defined herein; and pharmaceutically acceptable salts and individual diastereomers thereof.

Another embodiment of the present invention includes compounds of the formula Ia, wherein $R^7$ is heterocycle, unsubstituted or substituted with one or substituents independently selected from:
a) $C_{1-6}$ alkyl,
b) $C_{1-6}$ alkoxy,
c) fluorine,
d) HO,
e) $OR^5$,
f) $CO_2R^4$,
g) $CON(R^4)_2$,
h) $S(O)_m R^5$, and
i) $N(R^4)_2$; and and wherein $R^1$, $R^2$, $R^3$, $R^6$, G, J, Q, T, U, V and W are as defined herein; and pharmaceutically acceptable salts and individual diastereomers thereof.

A further embodiment of the present invention includes compounds of the formula Ib:

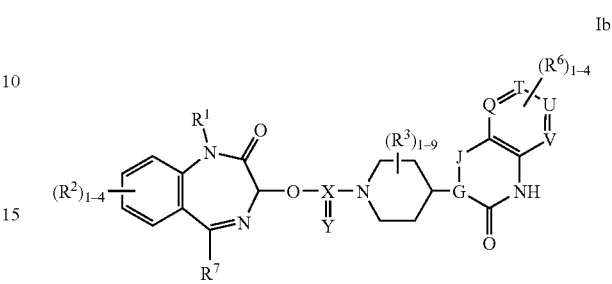

Ib wherein $R^1$, $R^2$, $R^3$, $R^6$, $R^7$, G, J, Q, T, U, V, X and Y are as defined herein; and pharmaceutically acceptable salts and individual diastereomers thereof.

A further embodiment of the present invention includes compounds of the formula Ic:

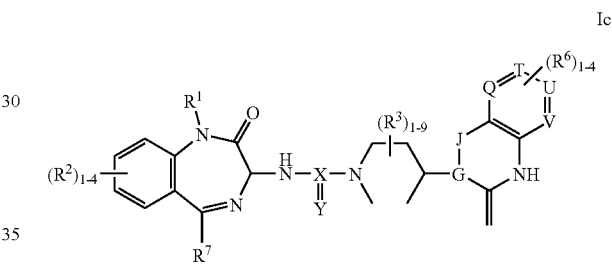

Ic wherein $R^1$, $R^2$, $R^3$, $R^6$, $R^7$, G, X, Q, T, U, V, X and Y are as defined herein; and pharmaceutically acceptable salts and individual diastereomers thereof.

An even further embodiment of the present invention includes compounds of the formula Id:

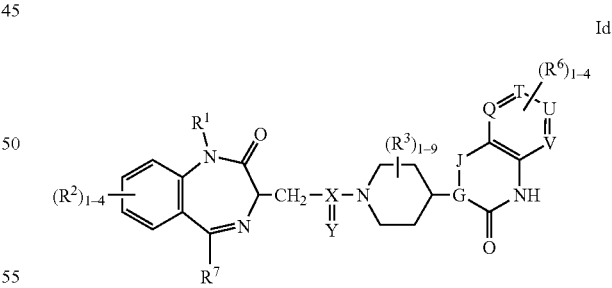

Id wherein $R^1$, $R^2$, $R^3$, $R^6$, $R^7$, G, J, Q, T, U, V, X and Y are as defined herein; and pharmaceutically acceptable salts and individual diastereomers thereof.

It is to be understood that where one or more of the above recited structures or substructures recite multiple substituents having the same designation each such variable may be the same or different from each similarly designated variable. For example, $R^2$ is recited four times in formula I, and each $R^2$ in formula I may independently be any of the substructures defined under $R^2$. The invention is not limited to structures and substructures wherein each $R^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, and that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxyrnaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_pC_{1-3}$ alkyl" this means that when there is one carbon, there are 2(1)+1=3 fluorines. When there are two carbons, there are 2(2)+1=5 fluorines, and when thre are three carbons there are 2(3)=1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CORP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 3944). Briefly, membranes (25 µg) were incubated in I ml of binding buffer [10 mM HEPES, pH 7.4, 5 mM $MgCl_2$ and 0.2% bovine serum albumin (BSA)] containing 10 pM $^{125}$I-CGRP andantagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 µg/ml streptomycin at 37° C., 95% humidity, and 5% $CO_2$. For cAMP assays, cells were plated at $5\times10^5$ cells/well in 96-well poly- D-lysine-coated plates (Becton-Dickinson) and cultured for ~18 h before assay. Cells were washed with phosphate-buffered saline (PBS, Sigma) then pre-incubated with 300 µM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) Br. J. Pharmacol. 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)^{nH}}$$

Where Y is observed CPM bound, $Y_{max}$ is total bound counts, Y min is non specific bound counts, (Y max−Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human A-CGRP was added to the cells at a concentration of 0.3 nM and allowed to incubate at 37° C. for 5 min. After A-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and IC$_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compounds of the following examples had activity as antagonists of the CGRP receptor in the aforementioned assays, generally with a $K_i$ or IC$_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a $^5$-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; anantidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamnine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT, agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of intermediates useful in the preparation of the compounds of the invention may be conducted as described in Schemes 1-7.

The preparation of final compounds proceeds through intermediates such as those of formulae II and III. Compounds of general formulae II and III are commercially available, known in the literature or may be conveniently prepared by a variety of methods familiar to those skilled in the art.

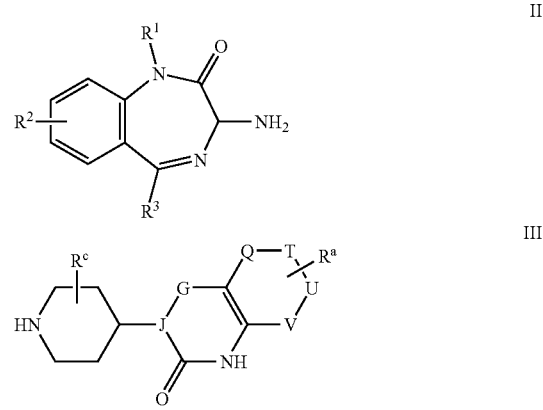

Representative syntheses for 3-amino-1,4-benzodiazepin-2-ones include Bock et al., Tetrahedron Lett, 1987, 28, 939-942; Bock et al., J. Org. Chem., 1987, 52, 3232-3239; Sherrill et al., J. Org. Chem. 1995, 60, 730-734; Butcher et al, Tetrahedron Lett. 1996, 37, 6685-6688; and Selnick et al., J. Med. Chem. 1997, 40, 3865-3868. When the 3-amino group in formula II is protected, for example with a carbonylbenzyloxy or t-butoxycarbonyl protecting group, the amide group ($R^1$=H) can be selectively reacted with an alkylating agent using various bases and solvents, including sodium hydride or cesium carbonate in a polar aprotic solvent like dimethylformamide. Subsequent deprotection produces the requisite 3-amino-1,4-benzodiazepin-2-one intermediate (Scheme 1).

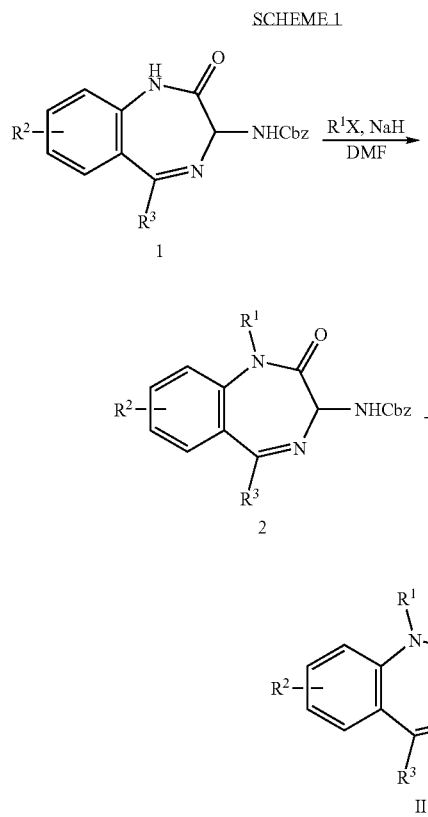

Chiral resolution of the amine intermediate can be accomplished by a number of methods, including those described by Rittle et al., Tetrahedron Lett., 1987, 28, 521-522; Reider, Chem. & Indus. 1988, 12, 394-398; Reider et al., J. Org. Chem. 1987, 52, 955-957; Sherrill et al., J. Org. Chem. 1995, 60, 730-734; Shi et al., Tetrahedron, 1999, 55, 909-918.

Aminobenzodiazepine II is converted to the 4-nitrophenylcarbamate 3, which is subsequently reacted with Intermediate III to form urea 4, as described in Scheme 2. Other activated intermediates known to those skilled in the art can be used to prepared compounds like 4.

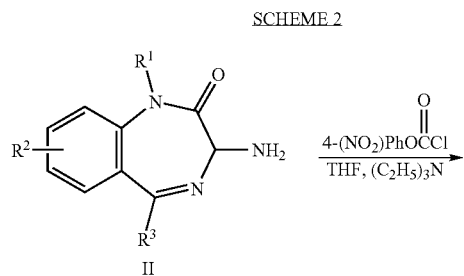

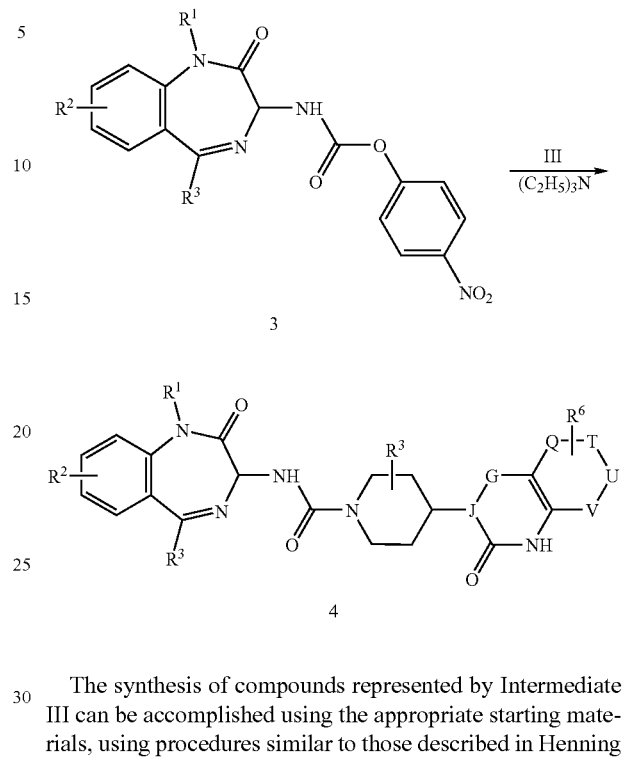

The synthesis of compounds represented by Intermediate III can be accomplished using the appropriate starting materials, using procedures similar to those described in Henning et al., J. Med. Chem., 1987, 30, 814-819; Carpino et al., WO 96/35713; Brown et al., J. Chem. Soc. 1957, 682-686; Barlin et al., Aust. J. Chem. 1982, 35 (11), 2299-2306; and references cited therein.

Additionally, the synthesis of compounds represented by Intermediate III can be accomplished by the Schemes described below. 5 For example, a diamino heterocycle, such as 2,3-diaminopyridine 5 in Scheme 3, can be reductively alkylated with ketones such as 6 to give the monalkylated product 7. Ring closure with carbonyldiimidazole furnishes imidazolone 8. Final deprotection and reaction with benzodiazepine 3 under standard conditions gives the final product 10.

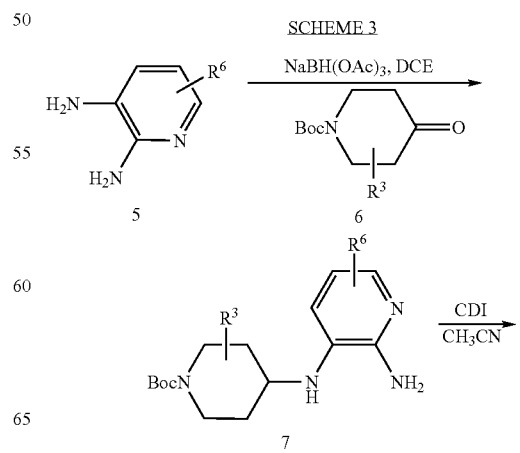

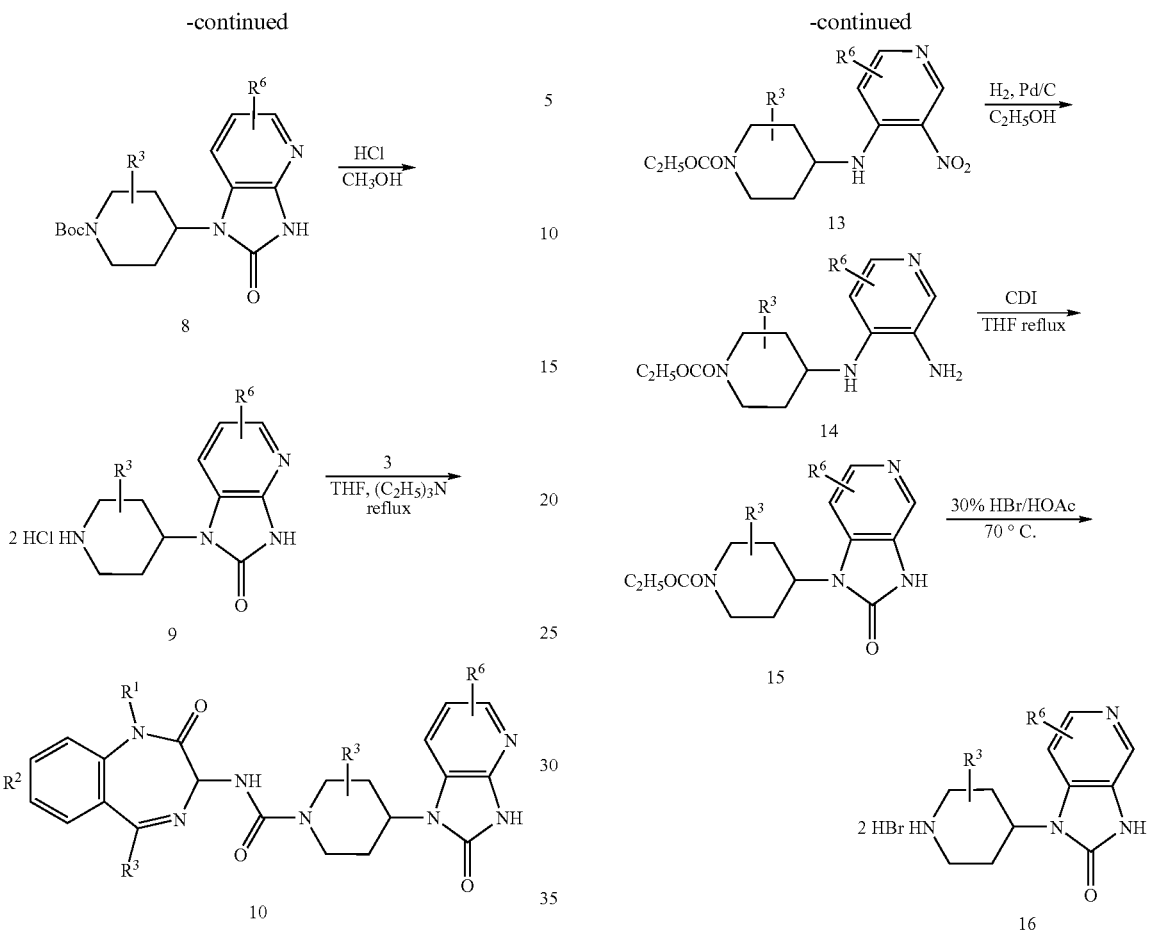

Alternatively, as described in Scheme 4, a suitably protected 4-aminopiperidine like 11 can be arylated by a number of methods, including palladium catalyzed arylation by the appropriate heteroaryl halide or equivalent, for example by 4-bromopyridine, which then would furnish 12. Nitration under standard conditions yields 13, which can be reduced to amine 14 by many methods, including catalytic hydrogenation. Acylation of 14 with carbonyldiimidazole is accompanied by ring closure to 15. Removal of the protecting group gives compounds like 16.

In Scheme 5, a suitably protected 4-aminopiperidine 17 can be arylated by an SNAr reaction, for example using methyl 2-bromopyrazine-3-carboxylate. The resulting product 18 can be converted to an acyl azide via acyl hydrazide 19. Thermal rearrangement of the acyl azide (Curtius rearrangement) can occur with concomitant ring closure to produce 20. Final deprotection under standard conditions gives the desired heterocycles 21.

SCHEME 4

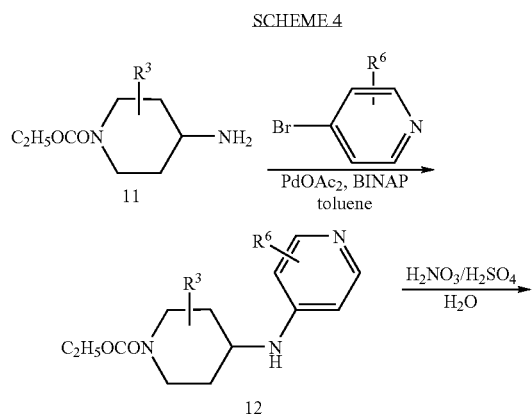

SCHEME 5

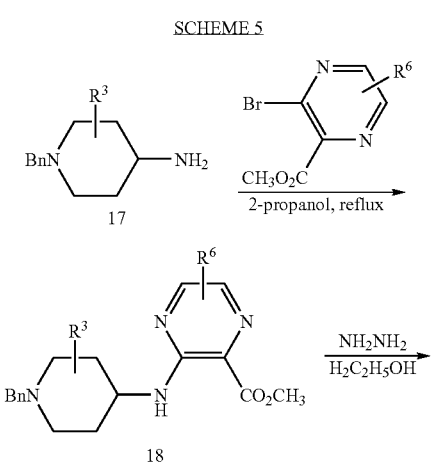

-continued

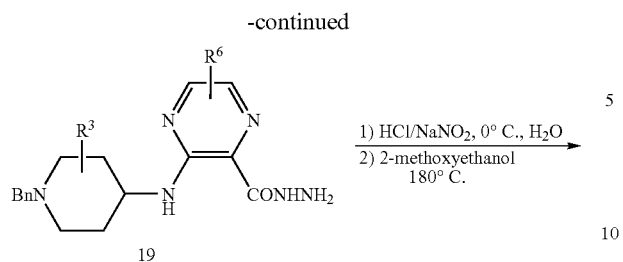

19

1) HCl/NaNO₂, 0° C., H₂O
2) 2-methoxyethanol
180° C.

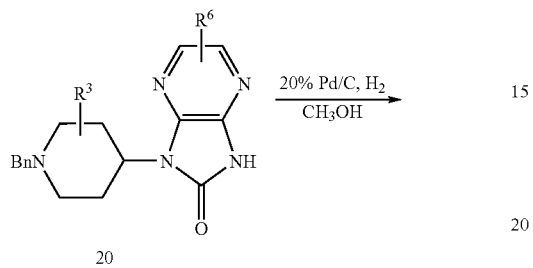

20

20% Pd/C, H₂
CH₃OH

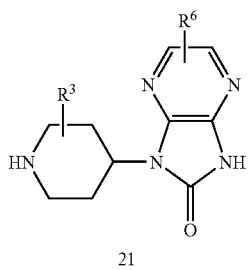

21

Additional heterocycles can be synthesized in a similar manner. For example, a heterocycle carboxaldehyde, such as 22 (*J. Med. Chem.* 1998, 31, 213645) in Scheme 6, can be reductively aminated with amines such as 23 to give the monalkylated product 24. Deprotection with acid and ring closure with carbonyldiimidazole furnishes pyridodihydropyrimidinone 26. Final deprotection under standard basic conditions gives the product 27.

SCHEME 6

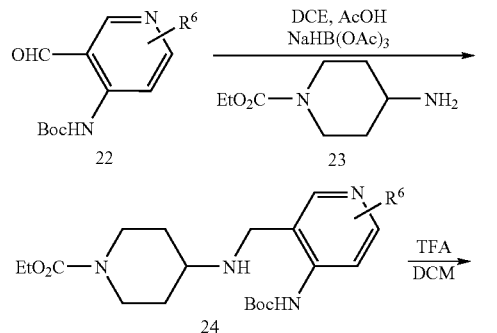

-continued

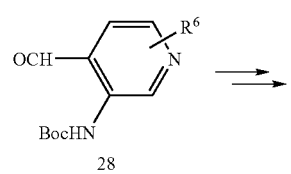

26

1N NaOH
reflux

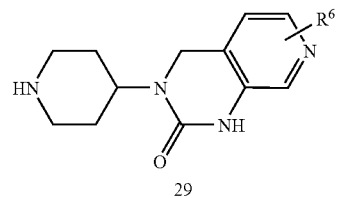

27

A similar synthetic strategy can be used to construct the related pyridodihydropyrimidinone of formula 29 starting from the commercially available aldehyde 28.

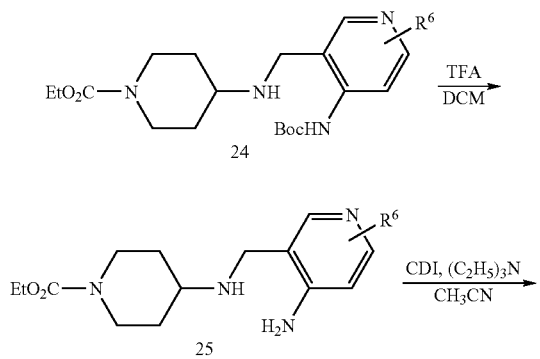

28

29

Alternatively, addition of a suitably protected amine, such as 31, to the commercially available chloropyridine 30, followed by nitrile reduction affords the diamine 33. This diamino heterocycle can be reductively alkylated with ketones such as 6 to give the monalkylated product 34. Ring closure with carbonyldiimidazole furnishes pyridodihydropyrimidinone 35. Final deprotection with trifluoroacetic acid gives the product 36.

SCHEME 7

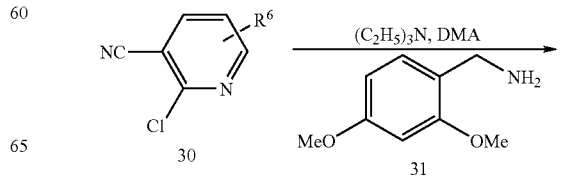

30    31

(C₂H₅)₃N, DMA

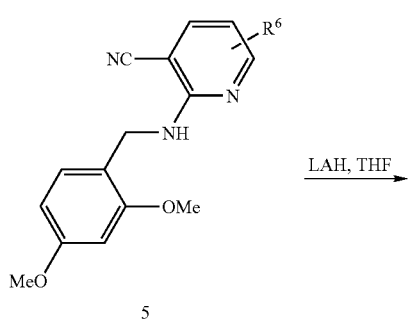

5

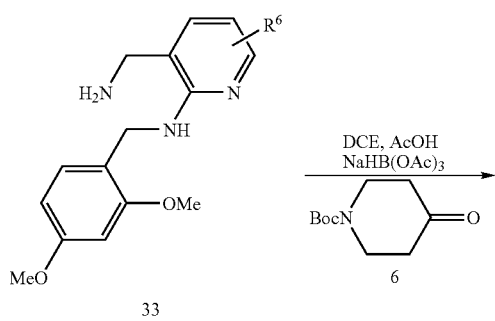

33

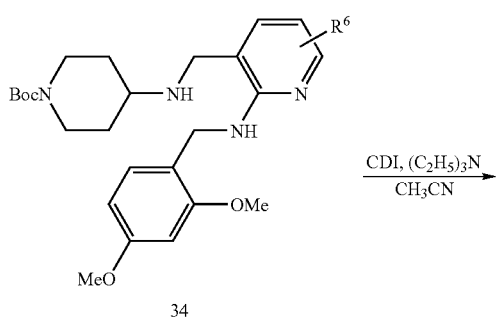

34

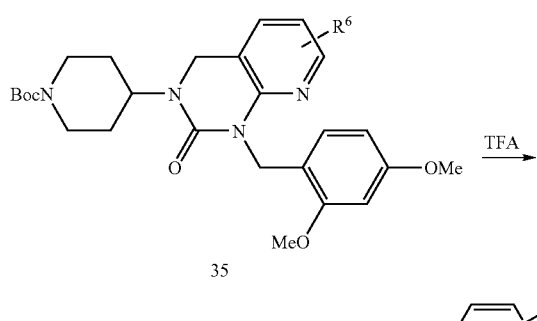

35

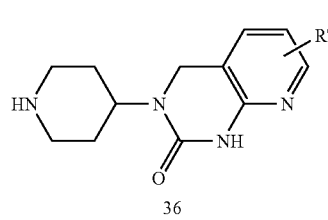

36

A similar synthetic strategy can be used to construct the related pyridodihydropyrimidinone of formula 38 starting from the known nitrite 37

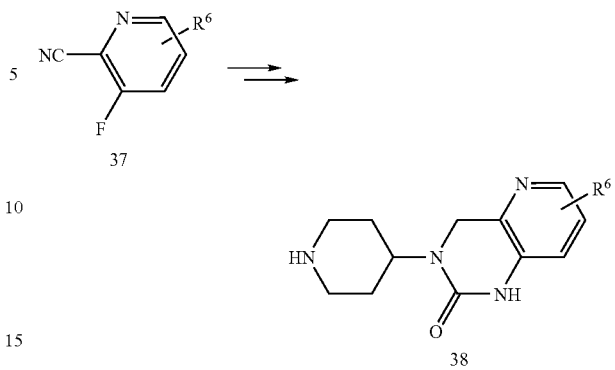

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate 1

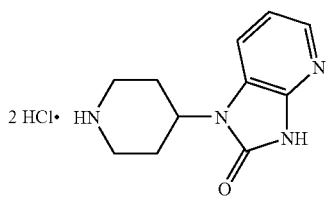

2-Oxo-1-(4-piperidinyl)-2,3-dihydro-1H-imidazo[4,5-b]pyridine dihydrochloride

Step A. 2-Amino-3-[(1-t-butoxycarbonylpiperidin-4-yl)amino)pyridine

Sodium triacetoxyborohydride (14.5 g, 68.7 mmol) was added to a solution of 2,3-diaminopyridine (5.00 g, 45.8 mmol) and N-(t-butoxycarbonyl)4-piperidone (9.58 g, 48.1 mmol) in dichloroethane (75 mL) at room temperature. After 5 h, additional sodium triacetoxyborohydride was added (1.8 g) and again after another 2.5 h. The reaction was stirred overnight, and quenched with 5% aqueous sodium hydroxide. This was extracted with methylene chloride, and washed with 5% aqueous sodium hydroxide, water and saturated sodium chloride solution. After drying over sodium sulfate, the solution was filtered and evaporated to give the crude product. This was purified by chromatorgraphy (silica gel, 3 to 5% methanol in methylene chloride gradient elution), which gave the title compound (4.44 g). MS 293 (M+1) $^1$H NMR (500 MHz, $C_3OD$) δ 7.32 (dd, J=1,5 Hz, 1H), 6.85 (dd, J=1, 8 Hz, 1H), 6.59 (dd, J=5, 8 Hz, 1H), 4.04 (d, J=13 Hz, 2H), 3.46 (m, 1H), 2.98 (br s, 2H), 2.01 (dd, J=2, 12 Hz, 2H), 1.46 (s, 9H), 1.37 (qd, J=4, 12 Hz, 2H).

Step B. 2-Oxo-1-(1-t-butoxycarbonylpiperidin-4-yl)-2,3-dihydro-1H-imidazo[4,5-b]pyridine Carbonyldiimidazole (0.70 g, 4.33 mmol) was added to a solution of 2-amino-3-[(1-t-butoxycarbonylpiperidin-4-yl)amino]pyridine (1.15 g, 3.93 mmol) in acetonitrile (150 mL) at room temperature. After several hours, an additional amount of carbonyldiimidazole was added (0.81 g), and the reaction stirred overnight. The acetonitrile was evaporated in vacuo, the residue partitioned between water and chloroform, and the organic phase washed with saturated brine and dried over magnesium sulfate. The crude product was purified by chromatorgraphy (silica gel, 1.2 to 2.5% methanol in methylene chloride gradient elution), which gave the title compound (1.09 g). $^1$H NMR (500 MHz, CDCl$_3$) δ 9.39 (br s, 1H), 8.04 (dd, J=1, 5 Hz, 1H), 7.33 (dd, J=1, 8 Hz, 1H), 6.99 (dd, J=5, 8 Hz, 1H), 4.50 (m, 1H), 4.32 (br s, 2H), 2.86 (br s, 2H), 2.20 (m, 2H), 1.86 (d, J=12 Hz, 2H), 1.50 (s, 9H).

Step C. 2-Oxo-1-(4-piperidinyl)-2,3-dihydro-1H-imidazo[4,5-b]pyridine dihydrochloride 2-Oxo-1-(1-t-butoxycarbonylpiperidin-4-yl)-2,3dihydro-1H-imidazo[4,5-b]pyridine (1.03 g, 3.23 mmol) was dissolved in methanol (25 mL) and a solution of 2N hydrochloric acid in ether (8 mL) was added at room temperature. After 2 h, the volatiles were removed in vacuo, to give the title compound (0.92 g). MS 219 (M+1). $^1$H NMR (500 MHz, C$_3$OD) δ 8.01 (dd, J=1,6 Hz, 1H), 7.83 (d, J=8 Hz, 1H), 7.28 (dd, J=6, 8 Hz, 1H), 4.60 (m, 1H), 3.59 (d, J=12 Hz, 2H), 3.21 (t, J=12 Hz, 2H), 2.70 (dq, J=4, 13 Hz, 2H), 2.12 (d, J=13 Hz, 2H).

Intermediate 2

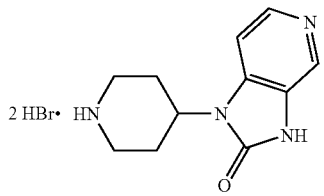

2Oxo-3-(4-piperidinyl)-2,3-dihydro-1H-imidazo[4,5-c]pyridine dihydrobromide

Step A. Ethyl 4-(pyridin4-ylamino)piperidine-1-carboxylate

A solution of ethyl 4-aminopiperidine-1-carboxylate (2.20 g, 12.7 mmol), 4-bromopyridine (3.47 g, 17.8 mmol), sodium t-butoxide (4,54 g, 47.2 mmol), 2,2'-bis(diphenylphosphino)-1,1'-binaphthyl (0.398 g, 0.639 mmol) and palladium acetate (0.143 g, 0.639 mmol) in toluene (40 mL) was heated at 60° C. overnight. The reaction was cooled and partitioned between ethyl acetate and water. The aqueous layer was washed 3 times with methylene chloride, and the combined organic layers dried over sodium sulfate. The crude product was purified by chromatography (silica gel, 0 to 10% {15% ammonium hydroxide in methanol} in methylene chloride gradient elution), which gave the title compound (1.3 g, 41% yield).

Step B. Ethyl 4-[(3-nitropyrin-4-yl)amino]piperidine-1-carboxylate

A solution of ethyl 4-(pyridin-4-ylamino)piperidine-1-carboxylate (1.30 g, 5.21 mmol) in 90% sulfuric acid (17 mL) was cooled to 0° C. To this was added 70% nitric acid (1.2 mL) in 90% sulfuric acid (8 mL). The reaction was stirred at 0° C. for 1.5 h, then poured into ice water (150 mL). Solid sodium carbonate was added to render the solution basic. This mixture was extracted four times with methylene chloride, dried, filtered and concentrated. The crude product was purified by chromatography (silica gel, 0 to 10% {5% ammonium hydroxide in methanol} in methylene chloride gradient elution), which gave the title compound (1.09 g, 71% yield).

Step C. Ethyl 4-[(3-aminopyrin-4-yl)amino]piperidine-1-carboxylate

Ethyl 4-[(3-nitropyrin4-yl)amino]piperidine-1-carboxylate (1.09 g, 3.70 mmol) in ethanol was hydrogenated (1 atm hydrogen) over 30% palladium on carbon (300 mg) for 4 h. The reaction was filtered through celite and concentrated in vacuo, to give the title compound (0.98 g, 100%).

Step D. Ethyl 4-[(2-oxo-2,3-dihydro-1H-imidazol[4,5-c]pyridin-1-yl)piperidine-1-carboxylate A solution of ethyl 4-[(3-aminopyrin4-yl)amino]piperidine-1-carboxylate (0.98 g, 3.70 mmol) and carbonyldiimidazole (1.80 g, 11.1 mmol) in tetrahydrofuran (40 mL) was refluxed until starting material was consumed. The solvent was removed in vacuo and the crude product purified by chromatography (silica gel, 0 to 10% {5% ammonium hydroxide in methanol} in methylene chloride gradient elution). Fractions containing product were dissolved in methylene chloride and washed with saturated sodium carbonate to remove co-eluting imidazole. The organic phase was dried over sodium sulfate, filtered and concentrated to give the title compound (0.360 g, 33% yield).

Step E. 2-Oxo-1-(4-piperidinyl)-2,3-dihydro-1H-imidazol[4,5-c]pyridine dihydrobromide A solution of ethyl 4-[(2oxo-2,3-dihydro-1H-imidazol[4,5-c]pyridin-1-yl)piperidine-1-carboxylate (0.120 g, 0.413 mmol) in 30% hydrogen bromide/acetic acid (1 rnL) was heated at 70° C. overnight. The reaction was cooled and concentrated in vacuo. The resulting solid was triturated with methylene chloride and dried, giving the title compound (0.123 g, 78% yield). $^1$H NMR (500 MHz, C$_3$OD) δ 8.48 (d, J=6 Hz, 1H), 8.46 (s,1H), 7.94 (d, J=6 Hz, 1H), 4.80 (m, 1H), 3.60 (d, J=10 Hz, 2H), 3.30 (m, partially obscured by solvent peak), 2.81 (dq, J=4,12 Hz, 2H), 2.16 (d, J=12 Hz, 2H).

Intermediate 3

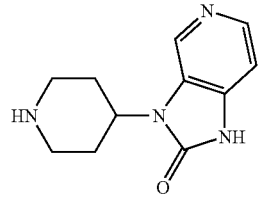

2-Oxo-3-(4-piperidinyl)-2,3-dihydro-1H-imidazo[4,5-c]pyridine

Step A. 4-Amino-3-[(1-benzylpiperidin-4-yl)amino)pyridine

A mixture of 3,4-diaminopyridine (1.1 g, 10.1 mmol), 1-benzyl-4-piperidone (3.2 g, 16.9 mmol) sodium triacetoxyborohydride (4.0 g, 18.9 mmol), and acetic acid (10.7 mL) in dichloroethane (10 mL) was stirred for about 6 days at room temperature. The reaction was concentrated to near dryness, and partitioned between chloroform (5×50 mL) and 1N sodium hydroxide (50 mL). The organic phase was dried over magnesium sufate and concentrated to give the title compound (2.8 g). MS 283 (M+1).

Step B. 2-Oxo-3-(1-benzylpiperidin4-yl)-2,3-dihydro-1H-imidazof4,5-c]pyridine A solution of 4-amino-3-[(1-benzylpiperidin-4-yl)amino)pyridine (2.8 g, 9.9 mmol) and carbonyldiimidazole (3.0 g, 18.5 mmol) in tetrahydrofuran (100 mL) was refluxed overnight. The reaction was cooled, concentrated and partitioned between chloroform (500 mL) and saturated sodium carbonate (100 mL). The organic phase was dried over magnesium sulfate and concentrated to give the title compound (2.8 g). MS 209 (M+1).

Step C. 2-Oxo-3-(4-piperidinyl)-2,3-dihydro-1H-imidazo[4,5-c]pyridine

A solution of 2-oxo-3-(1-benzylpiperidin-4-yl)-2,3-dihydro-1H-imidazo[4,5-c]pyridine (0.5 g, 1.6 mmol) in methanol (250 mL) was shaken with 20% Pd(OH)$_2$ under a hydrogen atmosphere for 48 h at room temperature. The reaction was filtered and concentrated to give the title compound as a white solid (0.3 g). MS 219 (M+1).

Intermediate 4

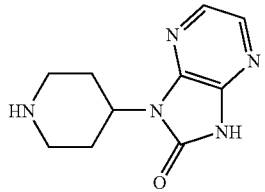

2-Oxo-1-(4-piperidinyl)-2,3-dihydro-1H-imidazo[4,5-b]pyrazine

Step A. Methyl 3-[(1-benzylpiperidin4-yl)amino]pyrazine-2-carboxylate

A mixture of methyl 2-bromopyrazine-3-carboxylate (J. Med. Chem., 1969, 12, 285) (2.2 g, 10.1 mmol) and 4-amino-1-benzylpiperidine (2.0 g, 10.5 mmol) was refluxed in 2-propanol overnight. Thin layer chromatography (10% methanol in ethyl acetate) showed the reaction was complete. The solvent was evaporated, and the crude product dissolved in chloroform (100 mL), which was washed with saturated sodium carbonate solution (20 mL), and dried over magnesium sulfate. The title compound was obtained as a gum (3.8 g). MS 327 (M+1).

Step B. 3-[(1-Benzylpiperidin-4-yl)amino]pyrazine-2-carbohydrazide

A mixture of methyl 3-[(1-benzylpiperidin-4-yl)amino]pyrazine-2-carboxylate (3.0 g, 9.2 mmol) and hydrazine hydrate (6 mL) in ethanol (100 mL) was refluxed with stirring for 2 h. The reaction was cooled and concentrated to give the title compound (3.0 g). MS 327 (M+1).

Step C. 2-Oxo-1-(1-benzylpiperidin-4-yl)-2,3-dihydro-1H-imidazo[4,5-b]pyrazine 3-[(1-Benzylpiperidin-4-yl)amino]pyrazine-2-carbohydrazide (3.0 g, 9.2 mmol) was dissolved in 1N HCl (20 mL) and water (40 mL), and cooled to 0° C. To this was added aqueous sodium nitrite (0.8 g, 11.6 mmol) in water (5 mL). After 0.5 h sodium bicarbonate was added and the basic solution extracted with chloroform (5×50 mL), which was dried over magnesium sulfate. The crude acyl azide was dissolved in methoxyethanol (20 mL) and heated at 180° C. for 3 h. The progress of the reaction was monitored by thin layer chromatography (10% methanol in chloroform). The reaction was cooled and concentrated, and the crude product purified by preparative thin layer chromatography (silica gel, 75:25 tetrahydrofuran:hexane) to give the title compound (1.7 g). MS 310 (M+1).

Step D. 2-Oxo-1-(4-piperidinyl)-2,3-dihydro-1H-imidazo[4,5-b]pyrazine

2-Oxo-1-(1-benzylpiperidin-4-yl)-2,3-dihydro-1H-imidazo[4,5-b]pyrazine (1.7 g, 5.5 mmol) was dissolved in methanol (100 mL) and hydrogentated over 20% palladium on carbon (0.5 g) at 55 psi hydrogen overnight. The catalyst was filtered and solvent evaporated to give the title compound (1.5 g).

Intermediate 5

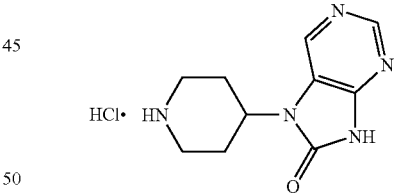

7-Piperidin-4-yl-7,9-dihydro-8H-purin-8-one hydrochloride

Step A. 4-Amino-5-[(1-t-butoxycarbonylpiperidin-4-yl)amino)pyrimidine

A mixture of 4,5-diaminopyrimidine (1.0 g, 9.1 mmol), N-(t-butoxycarbonyl)-4-piperidone (3.0 g, 15 mmol) and sodium triacetoxyborohydride (1.2 g, 5.6 mmol) in dichloroethane (60 mL) was stirred at room temperature for 3 d. The reaction was partitioned between chloroform (200 mL) and 3N sodium hydroxide (30 mL). After drying over magnesium sulfate, the organic phase was concentrated to give the title compound as a tan gum. MS 294 (M+1)

Step B. 7-(1-Benzylpiperidin-4-yl)-7,9-dihydro-8H-purin-8-one

The crude product from Step A, 4-amino-5-[(1-t-butoxycarbonylpiperidin-4-yl)amino)pyrimidine, was refluxed with carbonyldiimidazole (3.0 g, 18 mmol) in tetrahydrofuran (250 mL) for 2 d, cooled and concentrated. The crude product was dissolved in ethyl acetate (25-50 mL), which in four crops gave the title compound as a white crystalline solid (1.3 g). MS 320 (M+1)

Step C. 7-Piperidin-4-yl-7,9-dihydro-8H-purin-8-one hydrochloride

A mixture of 7-(1-benzylpiperidin-4-yl)-7,9-dihydro-8H-purin-8-one (1.2 g, 3.7 mmol) in 4N hydrogen chloride in dioxane (50 mL), was stirred vigorously at room temperature for 3 h. The reaction was concentrated in vacuo to give the title compound as a white solid. MS 220 (M+1)

Intermediate 6

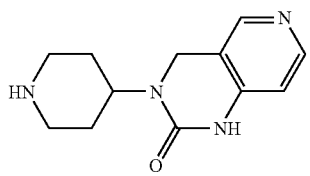

3-Piperidin-4-yl-3,4-dihydropyrido[4,3-d]pyrimidin-2(1H)-one

Step A. Ethyl 4-[({4-[(tert-butoxycarbonyl)amino]pyridin-3-yl}methyl)amino]piperidine-1-carboxylate Sodium triacetoxyborohydride (1.70 g, 8.03 mmol) and acetic acid (0.29, 4.82mmol) were added to a solution of N-Boc4-amino-3-pyridine carboxaldehyde (0.36 g, 1.61 mmol) and ethyl 4-aminopiperidine-1-carboxylate (0.33 g, 1.93 mmol) in dichloroethane (5 mL) at room temperature. The reaction was stirred overnight, and quenched with saturated aqueous sodium bicarbonate. This was separated, extracted with ethyl acetate and the combined organics were dried over sodium sulfate. The solution was filtered and evaporated to give the crude product. This was purified by chromatography (silica gel, 0 to 12% methanol in methylene chloride gradient elution), which gave the title compound (0.24 g). MS 379.2.

Step B. Ethyl 4-(2oxo-1,4dihydropyrido[4,3-d]pyrimidin-3(2H)-yl)piperidine-1-carboxylate Trifluoroacetic acid (0.50 mL) was a add to a solution of the material from Step A (0.24 g, 0.63 mmol) in dichloromethane (5 mL). After stirring overnight, another 0.5 mL of trifluoroacetic acid was added. After an additional 2 h, the reaction was concentrated. This material was dissolved in acetonitrile (5 mL) and carbonyldiimidazole (0.31 g, 1.89 mmol) was added at room temperature. After 2 h, the acetonitrile was evaporated in vacuo, the residue partitioned between 1N NaOH and dichloromethane, and the organic phase dried over magnesium sulfate. The crude product was purified by chromatography (silica gel, 10 to 15% methanol in methylene chloride gradient elution), which gave the title compound (0.089 g). MS 305.3.

Step C. 3-Piperidin-4-yl-3,4-dihydropyrido[4,3d]pyrimidin-2(1H)-one

Ethyl 4-(2-oxo-1,4-dihydropyrido[4,3-d]pyrimidin-3(2H)-yl)piperidine-1-carboxylate (0.089 g, 0.29 mmol) was diluted in 1N NaOH (5 mL) and heated to reflux. After 4 h, the reaction was concentrated in vacuo, the residue was diluted with MeOH: DCM, filtered and concentrated. The crude material was purified by reverse phase HPLC (C-18, 5% to 95% 0.1% trifluoroacetic acid/acetonitrile in 0.1% aqueous trifluoroacetic acid gradient elution) to give TFA salt of the title compound (0.12 g). MS 233.3 (M+1).

Intermediate 7

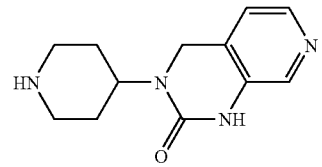

3-Piperidin-4-yl-3,4-dihydropyrido[3,4d]pyrimidin-2(1H)-one

Step A. Ethyl 4-[({3-[(tert-butoxycarbonyl)amino]pyridin-4-yl}methyl)amino]piperidine-1-carboxylate Sodium triacetoxyborohydride (0.57 g, 2.70 mmol) and acetic acid (0.41, 6.75 mmol) were added to a solution of N-Boc-3-amino-4-pyridine carboxaldehyde (0.50 g, 2.25 mmol) and ethyl 4-aminopiperidine-1-carboxylate (0.47 g, 2.70 mmol) in dichloroethane (5 mL) at room temperature. The reaction was stirred overnight, and quenched with saturated aqueous sodium bicarbonate. This was separated, extracted with ethyl acetate and the combined organics were dried over sodium sulfate. The solution was filtered and evaporated to give the crude product. This was purified by chromatography (silica gel, 1 to 12% methanol in methylene chloride gradient elution), which gave the title compound (0.47 g). MS 379.3.

Step B. Ethyl 4-(2-oxo-1,4-dihydropyrido[3,4-d]pyrimidin-3(2H)-yl)piperidine-1-carboxylate Trifluoroacetic acid (1,43 g) was a add to a solution of the material from Step A (0.47 g, 1.24 mmol) in dichloromethane (10 mL). After stirring overnight, the reaction was concentrated. This material was dissolved in acetonitrile (5 mL) and carbonyldiimidazole (0.62 g, 3.73 mmol) was added at room temperature. After 2 d, the acetonitrile was evaporated in vacuo, the residue partitioned between 1N NaOH and dichloromethane, and the organic phase dried over magnesium sulfate. The crude product was purified by chromatography (silica gel, 1 to 20% methanol in methylene chloride gradient elution), which gave the title compound (0.15 g). MS 305.2.

Step C. 3-Piperidin-4-yl-3,4-dihydropyrido[3,4-d]pyrimidin-2(1H)-one

Ethyl 4-(2-oxo-1,4-dihydropyrido[3,4-d]pyrimidin-3(2H)-yl)piperidine-1-carboxylate (0.15 g, 0.48 mmol) was diluted in 1N NaOH (10 mL) and heated to reflux. After 5 h, the reaction was concentrated in vacuo, the residue was diluted with MeOH: DCM, filtered and concentrated. The crude material was purified by reverse phase HPLC (C-18, 5% to 95% 0.1% trifluoroacetic acid/acetonitrile in 0.1% aqueous trifluoroacetic acid gradient elution) to give TFA salt of the title compound (0.17 g). MS 233.3 (M+1).

Intermediate 8

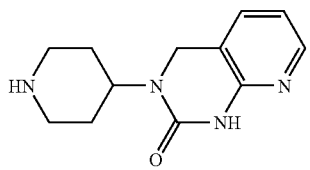

3-Piperidin-4-yl-3,4-dihydropyrido[2,3-d]pyrimidin-2(1H)-one

Step A. 2-[(2,4-dimethoxybenzyl)amino]nicotinonitrile 2,4-Dimethoxybenzylamine (2.90 g, 17.3 mmol) and triethylamine (1.75 g, 17.3 mmol) were added sequentially to a solution of 2chloronicotinonitrile (2.0 g, 14.4 mmol) in N,N-dimethylacetamide (29 mL). The reaction was heated at 80° C. for 4 h, quenched with water and extracted with diethyl ether (3×). The combined organic extracts were washed water, saturated brine, dried over magnesium sulfate and concentrated. The crude product was purified by flash chromatography (silica gel, 0-5% ethyl acetate (with 0.1 triethylamine) in dichloromethane gradient elution) to produce the title compound (2.80 g). MS 270.3 (M+1).

Step B. 3-(aminomethyl)-N-(2,4-dimethoxybenzyl)pyridin-2-amine

Lithium aluminum hydride (1.0 M in THF, 11.4 mL, 11.4 mmol) was added slowly to a solution of 2-[(2,4-dimethoxybenzyl)amino]nicotinonitrile (2.80 g, 10.4 mmol) in tetrahydrofuran (35 mL) at 0° C. The reaction was allowed to warm to room temperature and stir for 4 h. The reaction was carefully quenched with a saturated aqueous solution of sodium sulfate, filtered with copious dichloromethane and concentrated to produce the title compound (2.92 g). MS 274,3 (M+1).

Step C. tert-butyl 4-[({2-[(2,4-dimethoxybenzyl)amino]pyridin-3-yl}methyl)amino]piperidine-1-carboxylate Sodium triacetoxyborohydride (0.78 g, 3.66 mmol) and acetic acid (0.22 g, 3.66 mmol) were added to a solution of a portion of the material form Step B (1.00 g, <3.66 mmol) and N-(t-butoxycarbonyl)4-piperidone (0.73 g, 3.66 mmol) in dichloroethane (20 mL) at room temperature. After 3 h, the reaction was washed with saturated aqueous sodium bicarbonate, dried over sodium sulfate, the solution was filtered and evaporated to give the product (1.83 g). MS 457.3 (M+1).

Step D. tert-butyl 4-[1-(2,4-dimethoxybenzyl)-2-oxo-1,4-dihydropyrido[2,3-d]pyrimidin-3(2H)-yl]piperidine-1-carboxylate Carbonyldiimidazole (0.65 g, 4.0 mmol) was added to a solution of the material from Step C in dimethylformamide (20 mL) and the retain was heated to 150° C. After 1 d, further carbonyldiimidazole (0.65 g, 4.0 mmol) was added and the reaction heated for an additional 3 h. The reaction was diluted with water and extracted with dichloromethane, and the organic phase dried over sodium sulfate. The crude product was purified by chromatography (silica gel, 20 to 80% ethyl acetate in methylene chloride gradient elution), which gave the title compound (0.35 g). MS 483.3 (M+1).

Step E. 3-Piperidin-4-yl-3,4dihydropyrido[2,3-d]pyrimidin-2(1H)-one tert-Butyl 4-[1-(2,4-dimethoxybenzyl)-2-oxo-1,4-dihydropyrido[2,3d]pyrimidin-3(2H)-yl]piperidine-1-carboxylate (0.21 g, 0.43 mmol) was dissolved in trifluoroacetic acid (5 mL) and stirred overnight. The reaction was then heated to 50° C. for 3 h and concentrated to afford the bisTFA salt of the title compound (0.11 g). MS 233.3 (M+1).

Intermediate 9

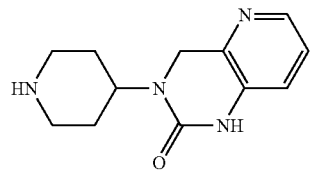

3-piperidin-4-yl-3,4-dihydropyrido[3,2-d]pyrimidin-2(1H)-one

Step A. 3-[(2,4dimethoxybenzyl)amino]pyridine-2-carbonitrile 2,4-Dimethoxybenzylamine (3.29 g, 19.7 mmol) and triethylamine (1.99 g, 19.7 mmol) were added sequentially to a solution of 2-cyano-3-fluoropyridine (2.0 g, 16.4 mmol) (Sakamoto et. al., *Chem. Pharm. Bull.*, 1985, 33, 565-71) in N,N-dimethylacetamide (29 mL). The reaction was heated at 80° C. for 4 h, quenched with water and extracted with diethyl ether (3×). The combined organic extracts were washed water, saturated brine, dried over magnesium sulfate and concentrated. The crude product was purified by flash chromatography (silica gel, 0-12% ethyl acetate (with 0.1 triethylamine) in dichloromethane gradient elution) to produce the title compound (3.25 g). MS 270.3 (M+1).

Step B. 2-(aminomethyl)-N-(2,4-dimethoxybenzyl)pyridin-3-amine

Lithium aluminum hydride (1.0 M in THF, 13.3 mL, 13.3 mmol) was added slowly to a solution of 3-[(2,4-dimethoxybenzyl)amino]pyridine-2-carbonitrile (3.25 g, 12.1 mmol) in tetrahydrofuran (40 mL) at 0° C. The reaction was warmed to room temperature and stirred for 4 h. The reaction was carefully quenched with a saturated aqueous solution of sodium sulfate, filtered with copious dichloromethane and concentrated to produce the title compound (2.68 g). MS 274,3 (M+1).

Step C. tert-butyl 4-[({3-[(2,4dimethoxybenzyl)amino]pyridin-2-yl}methyl)amino]piperidine-1-carboxylate Sodium triacetoxyborohydride (1.16 g, 5.49 mmol) and acetic acid (0.22 g, 3.66 mmol) were added to a solution of a portion of the material form Step B (1.72 g, 3.66 mmol) and N-(t-butoxycarbonyl)4-piperidone (0.88 g, 4,39 mmol) in dichloroethane (20 mL) at room temperature. After 3 h, the reaction was washed with saturated aqueous sodium bicarbonate, dried over sodium sulfate, the solution was filtered and evaporated to give the product (1.72 g). MS 457.3 (M+1).

Step D. tert-butyl 4-[1-(2,4-dimethoxybenzyl)-2-oxo-1,4-dihydropyrido[3,2-d]pyrimidin-3(2H)-yl]piperidine-1-carboxylate Carbonyldiimidazole (1.22 g, 7.53 mmol) was added to a solution of the material from Step C in dimethylformamide (20 mL) and the retain was heated to 150° C. overnight. The reaction was diluted with water and extracted with dichloromethane, and the organic phase dried over sodium sulfate. The crude product was purified by chromatography (silica gel, 30 to 100% ethyl acetate in methylene chloride gradient elution), which gave the title compound (0.10 g). MS 483.3 (M+1).

Step E. 3-piperidin-4-yl-3,4-dihydropyrido[3,2-d]pyrimidin-2(1H)-one tert-butyl 4-[1-(2,4-dimethoxybenzyl)-2-oxo-1,4-dihydropyrido[3,2-d]pyrimidin-3(2H)-yl]piperidine-1-carboxylate (0.10 g, 0.21 mmol) was dissolved in trifluoroacetic acid (5 mL) and stirred overnight. The reaction concentrated to afford the bisTFA salt of the title compound (0.048 g). MS 233.2 (M+1).

Intermediate 10

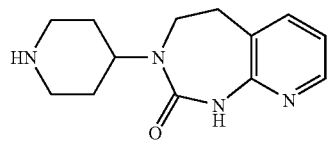

3-(4-Piperidinyl)-1,3,4,5-tetrahydro-2H-pyrido[2,3-d][1,3]diazapin-2-one hydrochloride Step A. 3-(2-Hydroxyethyl)-2-nitropyridine Dimethyl sulfide-borane complex (15.9 mL, 32 mmol) was added to a solution of 2-nitro-3-vinylpyridine (2.4 g, 15.9 mmol) (Yamaka et. al., *Heterocycles,* 1992, 34, 2379-2384) in tetrahydrofuran (30 mL) under argon. The reaction was stirred at 200C for 2 h, and concentrated in vacuo. The concentrate was redissolved in tetrahydrofuran and stirred overnight with 20% aqueous sodium hydroxide (20 mL) and 30% hydrogen peroxide solution (20 mL). Methylene chloride was added and the mixture extracted with saturated sodium bicarbonate, and the organic phase dried over sodium sulfate. The crude product was purified (silica gel, 0-50% ethyl acetate in hexane gradient elution) to produce the title compound (0.300 g). MS 169 (M+1).

Step B. 3-(2-Methansulfonyloxyethyl)-2-nitropyridine

Methane sulfonyl chloride (0.16 mL, 2.14 mmol) was added to a solution of 3-(2-hydroxyethyl)-2-nitropyridine (0.300 g, 1.78 mmol) and triethylamine (0.37 mL, 2.67 mmol) in methylene chloride (5 mL) at 0° C. under argon. After 1 h the reaction was worked up with saturated sodium bicarbonate and methylene chloride, and the organic phase dried over sodium sulfate and concentrated to give the title compound MS 247 (M+1).

Step C. 3-(2-Azidoethyl)-2-nitropyridine

Sodium azide (1.16 g, 17.8 mmol) was added to a solution of 3-(2-methansulfonyloxyethyl)-2-nitropyridine (0.44 g, 1.78 mmol) in dimethyl sulfoxide (5 mL), then stirred overnight at 50° C. The reaction was cooled and worked up with saturated sodium bicarbonate and methylene chloride. The organic phase was dried over sodium sulfate. This material was chromatographed (silica gel, 0-50% ethyl acetate in hexane, gradient elution) to produce the title compound (0.190 g) as a yellow oil. MS 194 (M+1).

Step D. 3-(2-Aminoethyl)-2-aminopyridine

A solution of 3-(2-azidoethyl)-2-nitropyridine (0.190 g, 0.98 mmol) in methanol (5 mL) was stirred at 20° C. with 10% palladium on carbon (50 mg) under 1 atm hydrogen for 96 h. The mixture was filtered through celite and the filtrate concentrated to give the title compound (0.122 g).

Step E. 3-[2-(1-t-Butoxycarbonyl-4-piperidinylamino)ethyl]-2-aminopyridine

A solution of 3-(2-aminoethyl)-2-aminopyridine (0.122 g, 0.88 mmol) and 1-t-butoxycarbonyl 4-piperidone (0.177 g, 0.88 mmol) in dichloroethane (3 mL) containing 2 drops of acetic acid was treated with sodium triacetoxyborohydride (0.28 g, 1.33 mmol) at 20-75° C. until starting material was no longer consumed. The reaction was worked up with saturated sodium bicarbonate and methylene chloride, and dried over sodium sulfate. The crude product was purified by chromatography (silica gel, 0-10% {0.1% ammonium hydroxide in methanol} in methylene chloride, gradient elution) to produce the title compound (0.119 g) as a yellow oil. MS 321 (M+1).

Step F. 3-[4-(1-t-Butoxycarbonylpiperidinyl)]-1,3,4,5-tetrahydro-2H-pyrido[2,3-d][1,3diazapin-2-one A solution of 3-[2-(1-t-butoxycarbonyl-4-piperidinylamino)ethyl]-2-aminopyridine (0.119 g, 0.37 mmol) and carbonyl diimidazole (0.152 g, 0.94 mmol) in acetonitrile (7 mL) was stirred at 20° C. under argon, until the reaction was complete. Sodium hydroxide was added (1 mL, 1M aqueous solution), and stirring continued for 30 min. The reaction was extracted with methylene chloride, dried and concentrated to give the title compound (144 mg) MS 347 (M+1).

Step G. 3-(4-Piperidinyl)-1,3,4,5-tetrahydro-2H-pyrido[2,3-d][1,3]diazapin-2-one hydrochloride A solution of 3-[4-(1-t-butoxycarbonylpiperidinyl)]-1,3,4,5-tetrahydro-2H-pyrido[2,3-d][1,3]diazapin-2-one (0.129 g, 0.37 mmol) in ethyl acetate (10 mL) was saturated with hydrogen chloride gas for 10 min. Concentration in vacuo provided the dihydrochloride salt of the title compound (0.118 g). MS 247 (M+1)

EXAMPLE 1

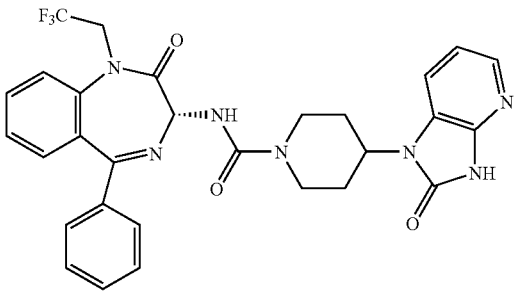

N-[(3R)-2-oxo-5-phenyl-1-(2,2,2-trifluoroethyl)-2,3-dihydro-1H-1,4-benzodiazepin-3-yl]4-(2-oxo-2,3-dihydro-1H-imidazo[4,5-b]pyridin-1-yl )piperidine-1-carboxamide A solution of (3R) 3-amino-2-oxo-5-phenyl-1-(2,2,2-trifluorethyl)-2,3-dihydro-1H-1,4-benzodiazepine (Y.-J. Shi et al., Tetrahedron, 1999, 55, 909-918) (0.150 g, 0.45 mmol) and 4-nitrophenylchloroformate (0.091 g, 0.45 mmol) in dry tetrahydrofuran (2.5 mL) was cooled to 0° C. under argon. Triethylamine (0.063 mL, 0.45 mmol) was added and the reaction stirred for 1 h. A solution of 2-oxo-1-(4-piperidinyl)-2,3-dihydro-1H-imidazo[4,5-b]pyridine dihydrochloride (0.130 g, 0.45 mmol) and triethylamine (0.190 mL) in dimethylsulfoxide (2.5 mL) was added. The reaction was allowed to come to room temperature and stirred overnight. The crude product was purified by reverse phase HPLC (C-18, 5% to 95% 0.1% trifluoroacetic acid/acetonitrile in 0.1% aqueous trifluoroacetic acid gradient elution). The pure fractions were extracted with methylene chloride and saturated sodium bicarbonate. The organic layer was dried, filtered and evaporated. The product was taken up in methanol and treated with hydrogen chloride. The solvent was evaporated and the resulting solid was dried in vacuo, to yield the title compound (184 mg, 66% yield). MS 578.2118 (M+1) $^1$H NMR (500 MHz, C$_3$OD) δ 8.02 (d, J=8 Hz, 1H), 8.00 (d, J=6 Hz, 1H), 7.80 (d, J=3 Hz, 2H), 7.60 (m, 3H), 7.50 (t, J=8 Hz, 2H), 7.45 (m, 1H), 7.39 (d, J=7 Hz, 1H), 7.34 (dd, J=6, 8 Hz, 1H), 5.55 (s, 1H), 5.26 (m, 1H), 4.61 (m, 2H), 4.35 (d, J=13 Hz, 2H), 3.08 (q, J=13 Hz, 2H), 2.40 (m, 2H), 1.91 (m, 2H).

EXAMPLE 2

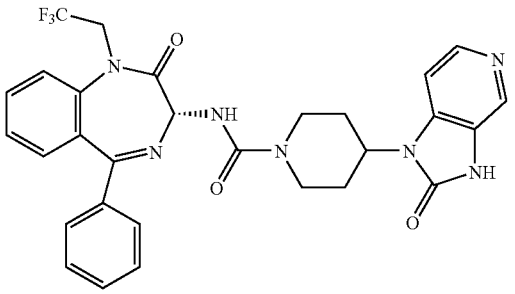

N-[(3R)-2-oxo-5-phenyl-1-(2,2,2-trifluoroethyl)-2,3-dihydro-1H-1,4-benzodiazepin-3-yl]4-(2-oxo-2,3-dihydro-1H-imidazo[4,5-c]pyridin-1-yl)piperidine-1-carboxamide A solution of (3R) 3-amino-2-oxo-5-phenyl-1-(2,2,2-trifluorethyl)-2,3-dihydro-1H-1,4-benzodiazepine (0.030 g, 0.090 mmol) and 4-nitrophenylchloroformate (0.018 g, 0.090 mmol) in dry tetrahydrofuran (0.5 mL) was cooled to 0° C. under argon. Triethylamine (0.013 mL, 0.090 mmol) was added and the reaction stirred for 1 h. A solution of 2-oxo-1-(4-piperidinyl)-2,3-dihydro-1H-imidazol[4,5-c]pyridine dihydrobromide (0.034 g, 0.90 mmol) and triethylamine (0.065 mL) in dimethylsulfoxide (0.5 mL) was added. The reaction was allowed to come to room temperature and stirred until complete. The crude product was purified by reverse phase HPLC (C-18, 5% to 95% 0.1% trifluoroacetic acid/acetonitrile in 0.1% aqueous trifluoroacetic acid gradient elution) to give the title compound (0.028 g, 45% yield). MS 578.2108 (M+1)

EXAMPLE 3

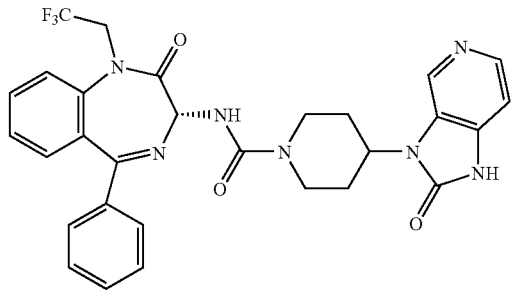

N-[(3R)-2-oxo-5-phenyl-1-(2,2,2-trifluoroethyl)-2,3-dihydro-1H-1,4-benzodiazepin-3-yl]4-(2-oxo-2,3-dihydro-1H-imidazo[4,5-c]pyridin-3-yl)piperidine-1-carboxamide The title compound was prepared from (3R) 3-amino-2-oxo-5-phenyl-1-(2,2,2-trifluorethyl)-2,3-dihydro-1H-1,4-benzodiazepine, and 2-oxo-3-(4-piperidinyl)-2,3-dihydro-1H-imidazo[4,5-c)pyridine, according to the procedure described in Examples 1 and 2 above. MS 578.214 (M+1)

EXAMPLE 4

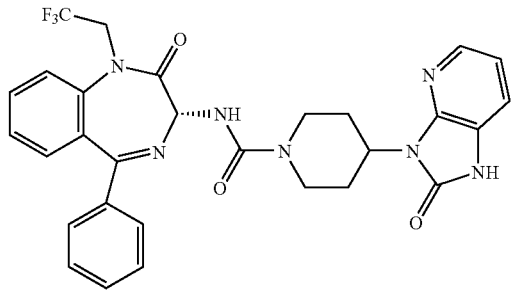

N-[(3R)-2-oxo-5-phenyl-1-(2,2,2-trifluoroethyl)-2,3-dihydro-1H-1,4-benzodiazepin-3-yl]4-(2-oxo-2,3-dihydro-1H-imidazo[4,5-b]pyridin-3-yl)piperidine-1-carboxamide The title compound was prepared from (3R) 3-amino-2-oxo-5-phenyl-1-(2,2,2-trifluorethyl)-2,3-dihydro-1H-1,4-benzodiazepine, and 2-oxo-3-(4-piperidinyl)-2,3-dihydro-1H-imidazo[4,5-b]pyridine (P. A. Carpino et al., WO 96/35713) according to the procedure described in Examples 1 and 2 above. MS 578.2118 (M+1)

EXAMPLE 5

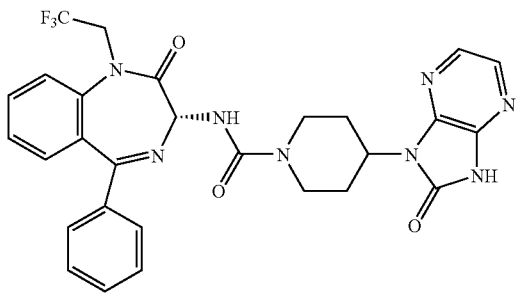

N-[(3R)-2-oxo-5-phenyl-1-(2,2,2-trifluoroethyl)-2,3-dihydro-1H-1,4-benzodiazepin-3-yl]4-(2,3-dihydro-1H-imidazo[4,5-b]pyrazin-1-yl)piperidine-1-carboxamide The title compound was prepared from (3R) 3-amino-2-oxo-5-phenyl-1-(2,2,2-trifluorethyl)-2,3-dihydro-H-1,4-benzodiazepine and 2-oxo-1-(4-piperidinyl)-2,3-dihydro-1H-imidazo[4,5-b]pyrazine, according to the procedure described in Examples 1 and 2 above. MS 561.1999 (M+1-$H_2O$)

EXAMPLE 6

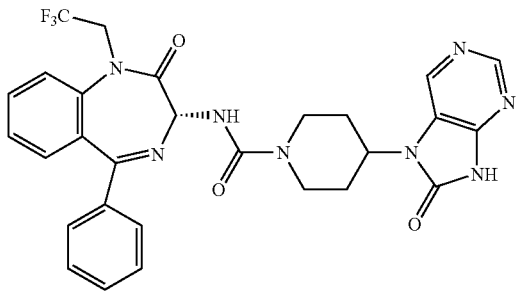

N-[(3R)-2-oxo-5-phenyl-1-(2,2,2-trifluoroethyl)-2,3-dihydro-1H-1,4-benzodiazepin-3-yl]4-(8-oxo-8,9-dihydro-7H-purin-7-yl)piperidine-1-carboxamide The title compound was prepared from (3R) 3-amino-2-oxo-5-phenyl-1-(2,2,2-trifluorethyl)-2,3-dihydro-1H-1,4-benzodiazepine and 7-piperidin-4-yl-7,9-dihydro-8H-purin-8-one hydrochloride, according to the procedure described in Examples 1 and 2 above. MS 561.1999 (M+K) 617.16663

EXAMPLE 7

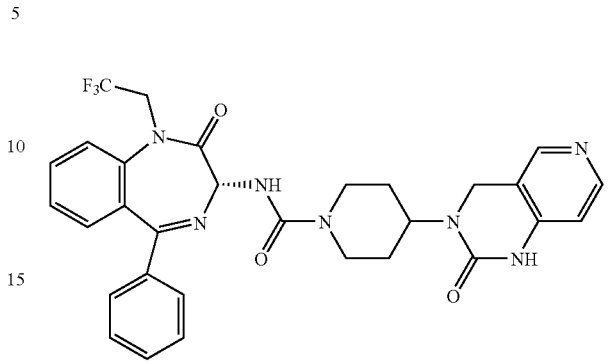

4(2-oxo-1,4-dihydropyrido[4,3-d]pyrimidin-3(2H)-yl)-N-[(3R)-2-oxo-5-phenyl-1-(2,2,2-trifluoroethyl)-2,3-dihydro-1H-1,4-benzodiazepin-3-yl]piperidine-1-carboxamide A solution of (3R) 3-amino-2-oxo-5-phenyl-1-(2,2,2-trifluorethyl)-2,3-dihydro-1H-1,4-benzodiazepine (0.030 g, 0.090 mmol) and 4-nitrophenylchloroformate (0.018 g, 0.090 mmol) in dry tetrahydrofuran (2 mL) was cooled to 0° C. under argon. Triethylamine (0.013 mL, 0.090 mmol) was added and the reaction stirred for 1 h. Solid 3-piperidin-4-yl-3,4-dihydropyrido[4,3-d]pyrimidin-2(1H)-one bisTFA salt (0.90 mmol) followed by triethylamine (0.065 mL) were added. The reaction was allowed to come to room temperature and stirred for 1 h. The reaction was quenched with 1N NaOH and concentrated. The crude product was purified by chromatography (silica gel, 0 to 15% methanol in methylene chloride gradient elution) to give the title compound (0.013 g, 24% yield). MS 592.2286 (M+1).

EXAMPLE 8

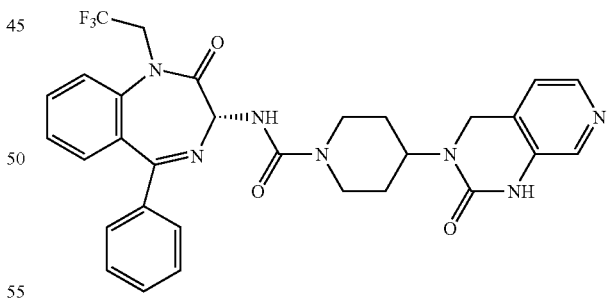

4-(2-oxo-1,4-dihydropyrido[3,4-d]pyrimidin-3(2H)-yl)-N-[(3R)-2-oxo-5-phenyl-1-(2,2,2-trifluoroethyl)-2,3-dihydro-1H-1,4-benzodiazepin-3-yl]piperidine-1-carboxamide A solution of (3R) 3-amino-2-oxo-5-phenyl-1-(2,2,2-trifluorethyl)-2,3-dihydro-1H-1,4-benzodiazepine (0.030 g, 0.090 mmol) and 4-nitrophenylchloroformate (0.018 g, 0.090 mmol) in dry tetrahydrofuran (2 mL) was cooled to 0° C. under argon. Triethylamine (0.013 mL, 0.090 mmol) was added and the reaction stirred for 1 h. Solid 3-piperidin4-yl-3,4-dihydropyrido[3,4-d]pyrimidin-2(1H)-one bisTFA salt (0.90 mmol) followed by triethylamine (0.065 mL) were added. The reaction was allowed to come to room temperature and stirred for 1 h. The reaction was quenched with 1N NaOH and concentrated. The crude product was purified by chromatography (silica gel, 0 to 10% methanol in methylene chloride gradient elution), to give the title compound (0.014 g, 27% yield). MS 592.2276 (M+1).

EXAMPLE 9

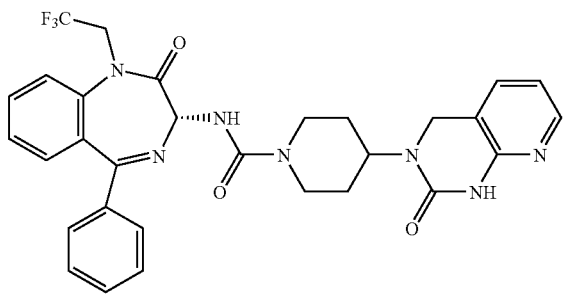

4-(2-oxo-1,4-dihydropyrido[2,3 d]pyrimidin-3(2H)-yl)-N-[(3R)-2-oxo-5-phenyl-1-(2,2,2-trifluoroethyl)-2,3-dihydro-1H-1,4-benzodiazepin-3-yl]piperidine-1-carboxamide A solution of (3R) 3-amino-2-oxo-5-phenyl-1-(2,2,2-trifluoroethyl)-2,3-dihydro-1H-1,4-benzodiazepine (0.037 g, 0.112 mmol) and 4-nitrophenylchloroformate (0.0238 g, 0.112 mmol) in dry tetrahydrofuran (2 mL) was cooled to 0° C. under argon. Triethylamine (0.011 g, 0.112 mmol) was added and the reaction stirred for 1 h. 3-Piperidin-4-yl-3,4-dihydropyrido[2,3-d]pyrimidin-2(1H)-one bisTFA salt (0.112 mmol) in DMSO (1 mL) followed by triethylamine (0.055 g) in were added. The reaction was allowed to come to room temperature and stirred for 4 h. The reaction was concentrated and purified by reverse phase HPLC (C-18, 5% to 95% 0.1% trifluoroacetic acid/acetonitrile in 0.1% aqueous trifluoroacetic acid gradient elution) to give TFA salt of the title compound (0.023 g, 29% yield). MS 592.2261 (M+1).

EXAMPLE 10

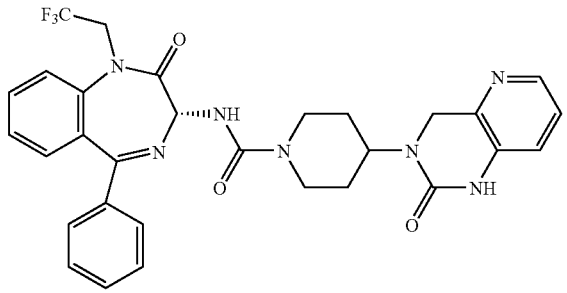

4-(2-oxo-1,4-dihydropyrido[3,2-d]pyrimidin-3(2H)-yl)-N-[(3R)-2-oxo-5-phenyl-1(2,2,2-trifluoroethyl)-2,3-dihydro-1H-1,4-benzodiazepin-3-yl]piperidine-1-carboxamide A solution of (3R) 3-amino-2-oxo-5-phenyl-1-(2,2,2-trifluoroethyl)-2,3-dihydro-1H-1,4-benzodiazepine (0.037 g, 0.112 mmol) and 4-nitrophenylchloroformate (0.0238 g, 0.112 mmol) in dry tetrahydrofuran (2 mL) was cooled to 0° C. under argon. Triethylamine (0.011 g, 0.112 mmol) was added and the reaction stirred for 1 h. 3-Piperidin-4-yl-3,4-dihydropyrido[3,2-d]pyrimidin-2(1H)-one bisTFA salt (0.103 mmol) in DMSO (1 mL) followed by triethylamine (0.055 g) were added. The reaction was allowed to come to room temperature and stirred for 4 h. The reaction was concentrated and purified by reverse phase HPLC (C-18, 5% to 95% 0.1% trifluoroacetic acid/acetonitrile in 0.1% aqueous trifluoroacetic acid gradient elution) to give TFA salt of the title compound (0.0123 g, 20% yield). MS 592.2308 (M+1).

EXAMPLE 11

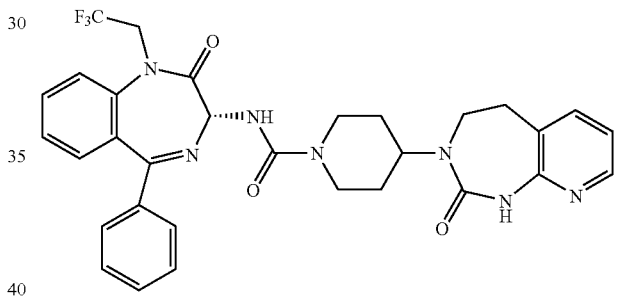

N-[3R)-2-oxo-5-phenyl-1-(2,2,2-trifluoroethyl)-2,3-dihydro-1H-1,4-benzodiazepin-3-yl]-4-(2-oxo-1,3,4,5-tetrahydro-2H-pyrido[2,3-d][1,3]diazepin-3-yl)piperidine-1-carboxamide A solution of (3R) 3-amino-2-oxo-5-phenyl-1-(2,2,2-trifluoroethyl)-2,3-dihydro-1H-1,4-benzodiazepine (0.015 g, 0.045 mmol) and 4-nitrophenylchloroformate (0.009 g, 0.045 mmol) in dry tetrahydrofuran (0.5 mL) was cooled to 0° C. under argon. Triethylamine (0.006 mL, 0.045 mmol) was added and the reaction stirred for 1 h. A solution of 3-(4-piperidinyl)-1,3,4,5-tetrahydro-2H-pyrido[2,3-d][1,3]diazapin-2-one dihydrochloride salt (0.014 g, 0.045 mmol) in dimethyl sulfoxide (0.5 mL) was added, followed by triethylamine (0.022 mL, 0.16 mmol). The reaction was allowed to come to room temperature and stirred overnight. The reaction was concentrated and purified by reverse phase HPLC (C-18, 5% to 95% 0.1% trifluoroacetic acid/acetonitrile in 0.1% aqueous trifluoroacetic acid gradient elution) to give the trifluoroacetic acid salt of the title compound (0.014 g). MS 606 (M+1).

What is claimed is:

1. A compound of formula I:

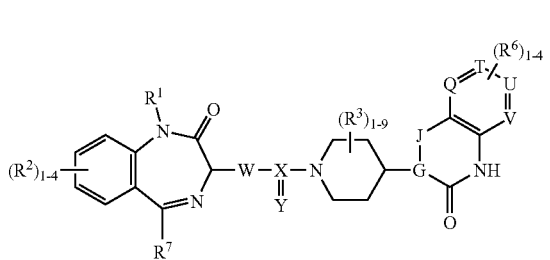

wherein:

R$^1$ is selected from:
1) H, C$_1$-C$_6$ alkyl, C$_2$-C$_6$ alkenyl, C$_2$-C$_6$ alkynyl, C$_3$-6 cycloalkyl, and heterocycle, unsubstituted or substituted with one or more substituents independently selected from:
   a) C$_{1-6}$ alkyl,
   b) C$_{3-6}$ cycloalkyl,
   c) aryl, unsubstituted or substituted with 1-5 substituents where the substituents are independently selected from R$^4$,
   d) heteroaryl, unsubstituted or substituted with 1-5 substituents where the substituents are independently selected from R$^4$,
   e) heterocycle, unsubstituted or substituted with 1-5 substituents where the substituents are independently selected from R$^4$,
   f) (F)$_p$C$_{1-3}$ alkyl,
   g) halogen,
   h) OR$^4$,
   i) O(CH$_2$)$_s$OR$^4$,
   j) CO$_2$R$^4$,
   k) (CO)NR$^{10}$R$^{11}$,
   l) O(CO)NR$^{10}$R$^{11}$,
   m) N(R$^4$)(CO)NR$^{10}$R$^{11}$,
   n) N(R$^{10}$)(CO)R$^{11}$,
   o) N(R$^{10}$)(CO)OR$^{11}$,
   p) SO$_2$NR$^{10}$R$^{11}$,
   q) N(R$^{10}$)SO$_2$R$^{11}$,
   r) S(O)$_m$R$^{10}$,
   s) CN,
   t) NR$^{10}$R$^{11}$,
   u) N(R$^{10}$)(CO)NR$^4$R$^{11}$, and
   v) O(CO)R$^4$; and
2) aryl or heteroaryl, unsubstituted or substituted with one or more substituents independently selected from:
   a) C$_{1-6}$ alkyl,
   b) C$_{3-6}$ cycloalkyl,
   c) aryl, unsubstituted or substituted with 1-5 substituents where the substituents are independently selected from R$^4$,
   d) heteroaryl, unsubstituted or substituted with 1-5 substituents where the substituents are independently selected from R$^4$,
   e) heterocycle, unsubstituted or substituted with 1-5 substituents where the substituents are independently selected from R$^4$,
   f) (F)$_p$C$_{1-3}$ alkyl,
   g) halogen,
   h) OR$^4$,
   i) O(CH$_2$)$_s$OR$^4$,
   j) CO$_2$R$^4$,
   k) (CO)NR$^{10}$R$^{11}$,
   l) O(CO)NR$^{10}$R$^{11}$,
   m) N(R$^4$)(CO)NR$^{10}$R$^{11}$,
   n) N(R$^{10}$)(CO)R$^{11}$,
   o) N(R$^{10}$)(CO)OR$^{11}$,
   p) SO$_2$NR$^{10}$R$^{11}$,
   q) N(R$^{10}$)SO$_2$R$^{11}$,
   r) S(O)$_m$R$^{10}$,
   s) CN,
   t) NR$^{10}$R$^{11}$,
   u) N(R$^{10}$)(CO)NR$^4$R$^{11}$, and
   v) O(CO)R$^4$; and R$^2$ is independently selected from H and:
1) C$_{1-6}$ alkyl,
2) C$_{3-6}$ cycloalkyl,
3) aryl, unsubstituted or substituted with 1-5 substituents where the substituents are independently selected from R$^4$,
4) heteroaryl, unsubstituted or substituted with 1-5 substituents where the substituents are independently selected from R$^4$,
5) heterocycle, unsubstituted or substituted with 1-5 substituents where the substituents are independently selected from R$^4$,
6) (F)$_p$C$_{1-3}$ alkyl,
7) halogen,
8) OR$^4$,
9) O(CH$_2$)$_s$OR$^4$,
10) CO$_2$R$^4$,
11) (CO)NR$^{10}$R$^{11}$,
12) O(CO)NR$^{10}$R$^{11}$,
13) N(R$^4$)(CO)NR$^{10}$R$^{11}$,
14) N(R$^{10}$)(CO)R$^{11}$,
15) N(R$^{10}$)(CO)OR$^{11}$,
16) SO$_2$NR$^{10}$R$^{11}$,
17) N(R$^{10}$)SO$_2$R$^{11}$,
18) S(O)$_m$R$^{10}$,
19) CN,
20) NR$^{10}$R$^{11}$,
21) N(R$^{10}$)(CO)NR$^4$R$^1$, and
22) O(CO)R$^4$;

R$^7$ is selected from:
1) H, C$_0$-C$_6$ alkyl, C$_2$-C$_6$ alkenyl, C$_2$-C$_6$ alkynyl, C$_{3-6}$ cycloalkyl and heterocycle, unsubstituted or substituted with one or more substituents independently selected from:
   a) C$_{1-6}$ alkyl,
   b) C$_{3-6}$ cycloalkyl,
   c) aryl, unsubstituted or substituted with 1-5 substituents where the substituents are independently selected from R$^4$,
   d) heteroaryl, unsubstituted or substituted with 1-5 substituents where the substituents are independently selected from R$^4$,
   e) heterocycle, unsubstituted or substituted with 1-5 substituents where the substituents are independently selected from R$^4$,
   f) (F)$_p$C$_{1-3}$ alkyl,
   g) halogen,
   h) OR$^4$,
   i) O(CH$_2$)$_s$OR$^4$,
   j) CO$_2$R$^4$,
   k) (CO)NR$^{10}$R$^{11}$,
   l) O(CO)NR$^{10}$R$^{11}$,
   m) N(R$^4$)(CO)NR$^{10}$R$^{11}$, n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_m R^{10}$,
s) CN,
t) $NR^{10}R^{11}$,
u) $N(R^{10})(CO)NR^4R^{11}$,
v) $O(CO)R^4$; and 2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_m R^{10}$,
   s) CN,
   t) $NR^{10}R^{11}$,
   u) $N(R^{10})(CO)NR^4R^{11}$, and
   v) $O(CO)R^4$;

$R^4$ is selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

$R^5$ is independently selected from H, substituted or unsubstituted $C_1$-$C_6$ alkyl, $C_{3-6}$ cycloalkyl, aryl, heteroaryl, $OR^4$, $N(R^4)_2$, $CO_2R^4$ and $(F)_p C_{1-6}$ alkyl;

W is O, $NR^4$ or $C(R^4)_2$;

X is C or S;

Y is O, $(R^4)_2$, NCN, $NSO_2CH_3$ or $NCONH_2$, or Y is $O_2$ when X is S;

$R^3$ is independently selected from H, substituted or unsubstituted $C_1$-$C_3$ alkyl, CN and $CO_2R^4$;

$R^6$ is independently selected from H and:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_m R^{10}$,
   s) CN,
   t) $NR^{10}R^{11}$,
   u) $N(R^{10})(CO)NR^4R^{11}$, and
   v) $O(CO)R^4$;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from $R^4$;

G-J is selected from: N, N—$C(R^5)_2$, $C=C(R^5)$, $C=N$; $C(R^5)$, $C(R^5)$—$C(R^5)_2$, $C(R^5)$—$C(R^5)_2$—$C(R^5)_2$, $C=C(R^5)$—$C(R^5)_2$, $C(R^5)$—$C(R^5)=C(R^5)$, $C(R^5)$—$C(R^5)_2$—$N(R^5)$, $C=C(R^5)$—$N(R^5)$, $C(R^5)$—$C(R^5)=N$, $C(R^5)$—$N(R^5)$—$C(R^5)_2$, $C=N$—$C(R^5)_2$, $C(R^5)$—$N=C(R^5)$, $C(R^5)$—$N(R^5)$—$N(R^5)$, $C=N$—$N(R^5)$, N—$C(R^5)_2$—$C(R^5)_2$, N—$C(R^5)=C(R^5)$, N—$C(R^5)_2$—$N(R^5)$, N—$C(R^5)=N$, N—$N(R^5)$—$C(R^5)_2$ and N—$N=C(R^5)$;

Q, T, U and V are each independently a carbon atom or a nitrogen atom wherein at least one but no more than three of Q, T, U and V are nitrogen atoms, and wherein when any of Q, T, U, or V is a carbon atom it is unsubstituted or substituted where the substituents are independently selected from $R^6$;

p is 0 to 2q+1, for a substituent with q carbons;

m is 0, 1 or 2;

n is 0 or 1;

s is 1, 2 or 3;

"heterocyclic" is a stable 5- to 7- membered monocyclic- or stable 8- to 11- membered bicyclic heterocyclic ring system, which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quarternized, and including any bicyclic group in which any of the above-defined heterocyclic rings is fused to a benzene ring;

"heteroaryl" is a stable 5- to 7- membered monoclcylic stable 9- to 10-membered fused bicyclic heterocyclic ring system which contains an aromatic ring, any ring of which may be saturated;

or a pharmaceutically acceptable salt or individual diastereomer thereof.

2. The compound of claim 1 of the formula Ia:

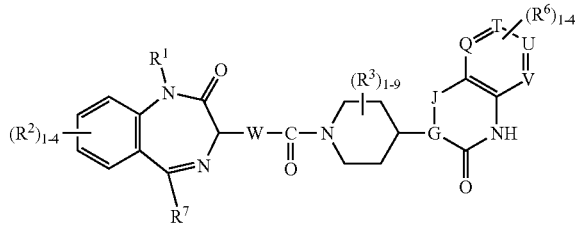

Ia or a pharmaceutically acceptable salt or individual diastereomer thereof.

3. The compound of claim 2, wherein $R^7$ is phenyl, unsubstituted or substituted with one or substituents independently selected from:
a) $C_{1-6}$ alkyl,
b) OH,
c) $OR^5$,
d) halogen,
e) $CO_2R^4$,
f) $S(O)_mR^5$,
g) $N(R^4)_2$, and
j) CN,
or a pharmaceutically acceptable salt or individual diastereomer thereof.

4. The compound of claim 2, wherein $R^7$ is heteroaryl, unsubstituted or substituted with one or substituents independently selected from:
a) $C_{1-6}$ alkyl,
b) OH,
c) $OR^5$,
d) halogen,
e) $CO_2R^4$,
f) $S(O)_mR^5$,
g) $N(R^4)_2$, and
j) CN,
or a pharmaceutically acceptable salt or individual diastereomer thereof.

5. The compound of claim 2, wherein $R^7$ is selected from H and $C_1$-$C_6$ alkyl, $C_1$-$C_6$ alkenyl, $C_1$-$C_6$ alkynyl, $C_3$-$C_6$ cycloalkyl, unsubstituted or substituted with one or substituents independently selected from:
a) $C_{1-6}$ alkyl,
b) $C_{1-6}$ alkoxy,
c) fluorine,
d) HO,
e) $OR^5$,
f) $CO_2R^4$,
g) $CON(R^4)_2$,
h) $S(O)_mR^5$, and
i) $N(R^4)_2$; and
or a pharmaceutically acceptable salt or individual diastereomer thereof.

6. The compound of claim 2, wherein $R^7$ is heterocycle, unsubstituted or substituted with one or substituents independently selected from:
a) $C_{1-6}$ alkyl,
b) $C_{1-6}$ alkoxy,
c) fluorine,
d) HO,
e) $OR^5$,
f) $CO_2R^4$,
g) $CON(R^4)_2$,
h) $S(O)_mR^5$, and
i) $N(R^4)_2$; and
or a pharmaceutically acceptable salt or individual diastereomer thereof.

7. The compound of claim 1 of the formula Ib:

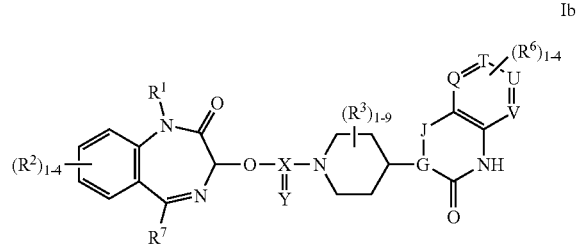

Ib or a pharmaceutically acceptable salt or individual diastereomer thereof.

8. The compound of claim 1 of the formula Ic:

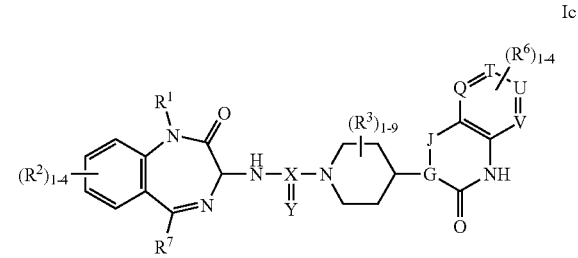

Ic or a pharmaceutically acceptable salt or individual diastereomer thereof.

9. The compound of claim 1 of the formula Id:

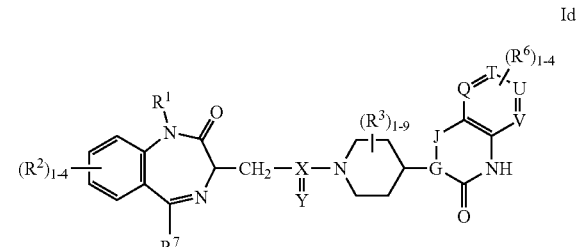

Id or a pharmaceutically acceptable salt or individual diastereomer thereof.

10. A compound selected from:

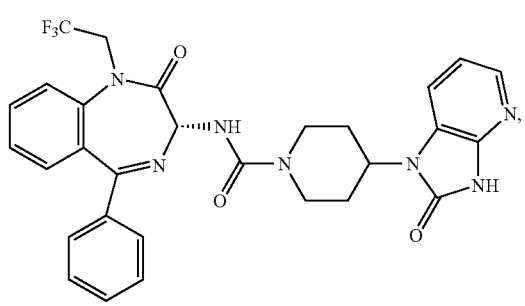

-continued

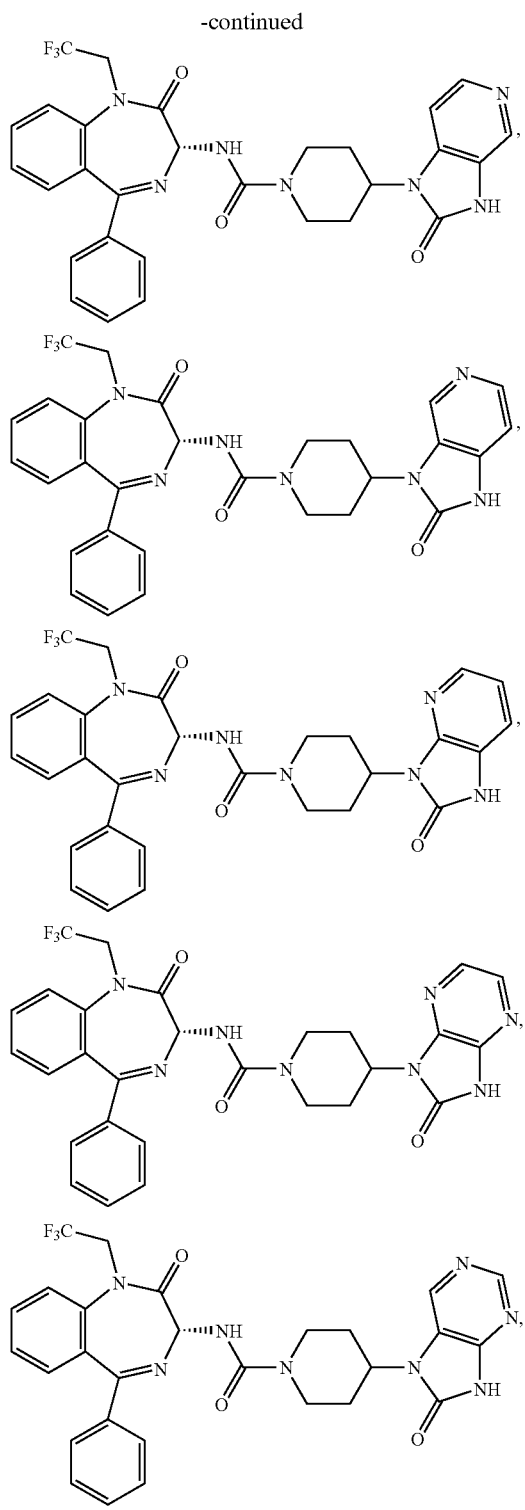

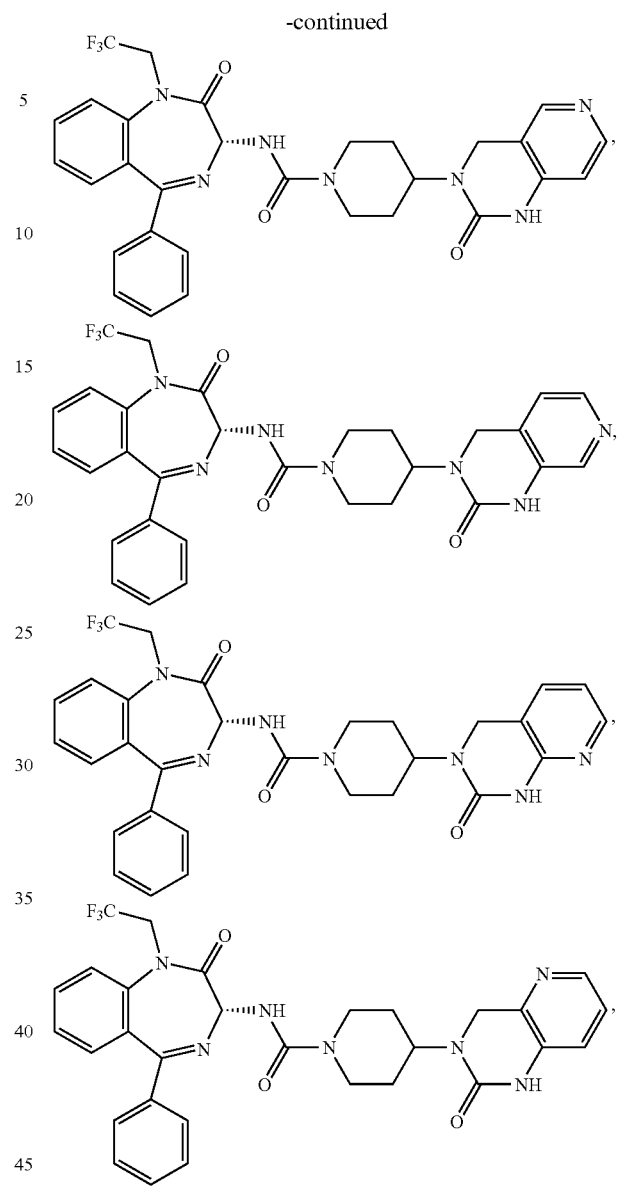

or a pharmaceutically acceptable salt or individual diastereomer thereof.

11. A pharmaceutical composition which comprises an inert carrier and the compound of claim 1.

12. A method for treating headache in a mammalian patient in need of such which comprises administering to the patient a therapeutically effective amount of the compound of claim 1.

13. The method of claim 12 wherein the headache is a migraine headache or cluster headache.

* * * * *